(12) United States Patent
Allessie et al.

(10) Patent No.: US 11,497,441 B2
(45) Date of Patent: Nov. 15, 2022

(54) SLEEP POSITION TRAINING DEVICE AND METHOD FOR CONTROLLING SUCH DEVICE

(71) Applicant: Side Sleep Technologies B.V., Amsterdam (NL)

(72) Inventors: Michiel Jeroen Allessie, Amsterdam (NL); Idan Reuven Velleman, Amsterdam (NL)

(73) Assignee: Side Sleep Technologies B.V., Amsterdam (NL)

( * ) Notice: Subject to any disclaimer, the term of this patent is extended or adjusted under 35 U.S.C. 154(b) by 23 days.

(21) Appl. No.: 16/745,715

(22) Filed: Jan. 17, 2020

(65) Prior Publication Data

US 2021/0100497 A1  Apr. 8, 2021

(30) Foreign Application Priority Data

Oct. 7, 2019 (NL) ........................... 2023972
Jan. 10, 2020 (NL) ........................... 2024650

(51) Int. Cl.
*A61B 5/00* (2006.01)
*A61B 5/11* (2006.01)
*A61M 21/00* (2006.01)

(52) U.S. Cl.
CPC ............... *A61B 5/486* (2013.01); *A61B 5/11* (2013.01); *A61B 5/4806* (2013.01);
(Continued)

(58) Field of Classification Search
CPC .......... A61B 5/486; A61B 5/11; A61B 5/4806
See application file for complete search history.

(56) References Cited

U.S. PATENT DOCUMENTS 5,081,447 A    1/1992 Echols
2003/0120183 A1*  6/2003 Simmons ................ G06F 3/011
                                                            600/595
(Continued)

FOREIGN PATENT DOCUMENTS

WO    2018182414 A1    10/2018

OTHER PUBLICATIONS

International Search Report issued in corresponding International Patent Application No. PCT/NL2020/050022, dated Aug. 5, 2020 (7 pages).
(Continued)

*Primary Examiner* — Alex M Valvis
*Assistant Examiner* — Yasmeen S Warsi
(74) *Attorney, Agent, or Firm* — Greenberg Traurig, LLP; Roman Fayerberg; Richard Brooks

(57) ABSTRACT

One aspect of this disclosure relates to a sleep position training device for reducing gastroesophageal reflux during sleep. The training device can comprise an orientation sensor, a stimulus generator and a processing system. The orientation sensor can be configured to output a signal indicative of an orientation of the torso of the person. The stimulus generator can be configured to provide a stimulus to the torso of the person when the torso of the person is in a predetermined torso orientation range in a sleeping position. The stimulus generator can be removably affixable to the torso of the person. The processing system can be configured to receive a first signal from the orientation sensor, the first signal being indicative of an orientation of the torso of the person, and to determine that the orientation is within the predetermined torso orientation range in the sleeping position.

19 Claims, 13 Drawing Sheets

(52) U.S. Cl.
CPC .......... *A61B 5/6823* (2013.01); *A61M 21/00* (2013.01); *A61B 2562/0219* (2013.01); *A61M 2021/0022* (2013.01)

(56) References Cited

U.S. PATENT DOCUMENTS

2015/0136146 A1    5/2015    Hood et al.
2019/0160282 A1    5/2019    Dieken et al.
2019/0231256 A1    8/2019    Jantunen

OTHER PUBLICATIONS

Written Opinion in International Patent Application No. PCT/NL2020/050022, dated Mar. 25, 2021 (9 pages).

* cited by examiner

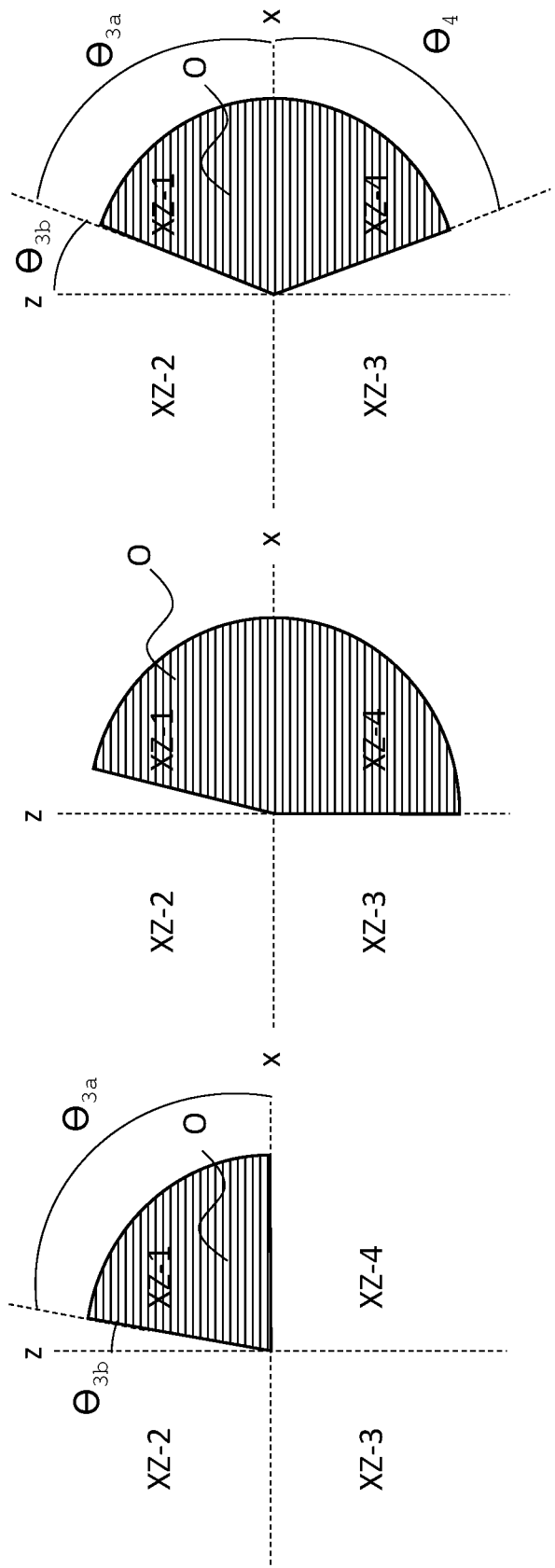

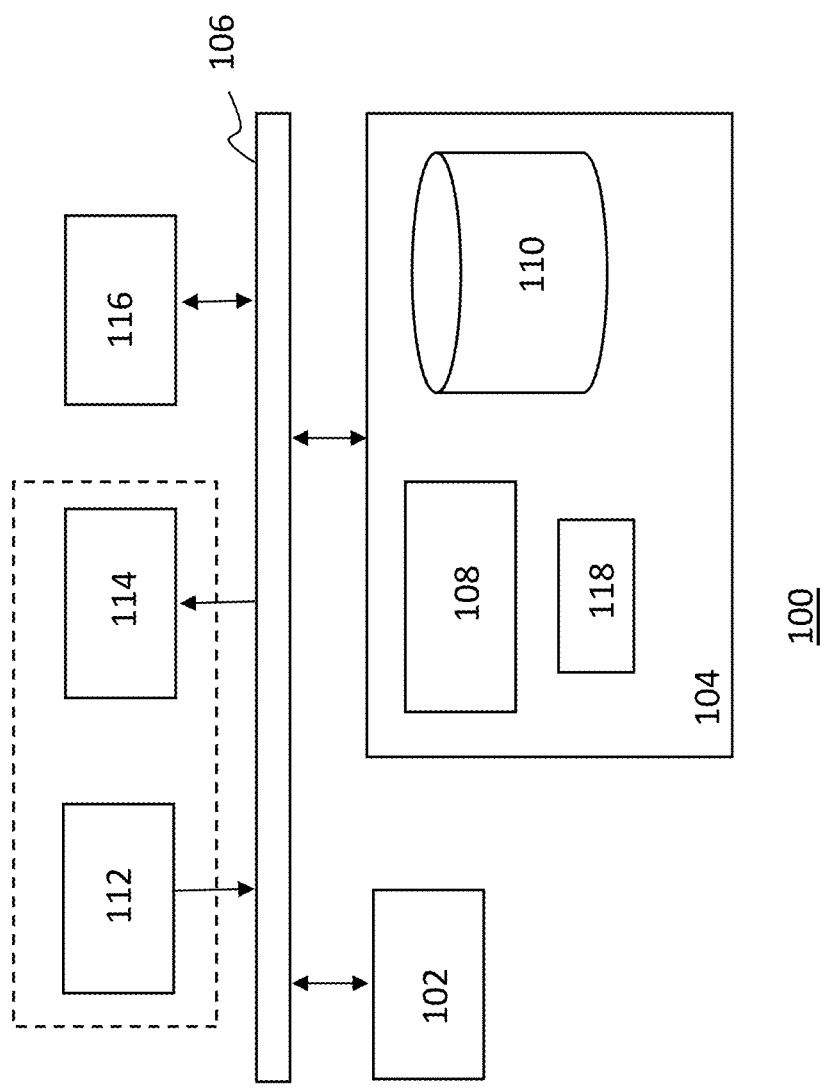

SLEEP POSITION TRAINING DEVICE AND METHOD FOR CONTROLLING SUCH DEVICE

CROSS REFERENCE TO RELATED APPLICATIONS

This application claims priority to Netherlands Application No. NL 2023972, filed on Oct. 7, 2020 and Netherlands Application No. NL 2024650, filed on Jan. 10, 2020, each of which are hereby incorporated by reference herein in their entireties.

FIELD

This disclosure relates to a sleep position training device, a method, computer program and computer-readable storage medium for controlling such device.

BACKGROUND

The sleep position of a person can have various health effects for that person, such as respiratory problems, snoring and occurrence of excessive gastroesophageal reflux. Special aids like mattresses and cushions have been developed to affect the sleeping position to reduce or avoid these effects.

Other aids are directed to training the person to assume a particular position by means of feedback to the person. Such sleep position training devices are known for snoring. For example, a positional snorer is somebody who snores mainly when sleeping on his back, i.e. when he is in the "supine position", causing the head to also be in a straight position (eyes facing the ceiling). If the head and/or body are in a supine position, the tongue falls in the airway more often because of gravity than when the person's head is tilted sideways or the person sleeps on his side. When the tongue is in the airway, it partially blocks the airway, which is an important cause of snoring.

Sleep position training may be used to train a person to not sleep in the supine position, but in another position that does not induce snoring. However, there is still a need for devices and methods for sleep position training that address other sleep conditions.

SUMMARY

One aspect of the present disclosure relates to a sleep position training device specifically designed for reducing (nocturnal) gastroesophageal reflux, also known as nighttime acid reflux, nighttime heartburn, or regurgitation during sleep when the person is in a substantially horizontal position, for example when the person is in bed. It should be appreciated that other indications related to the esophagus can benefit from the training device, including scleroderma, atresia and achalasia.

In some embodiments, the training device comprises an orientation sensor (e.g. a triaxial accelerometer), a stimulus generator (e.g. providing vibrations) and a processing system (e.g. a microprocessor configured to run certain code portions for the sleep position training).

The orientation sensor is configured to output a signal indicative of an orientation of the torso of the person, i.e. the part of the body between the head and the legs of the person.

The stimulus generator is configured to provide a first stimulus to the torso of the person to change the orientation of the torso of the person when the torso of the person is in a predetermined torso orientation range in a sleeping position. The stimulus generator is removably affixable to the torso of the person, e.g. by using a sticker.

The processing system is configured to receive a first signal from the orientation sensor, the first signal being indicative of an orientation of the torso of the person and to determine that the orientation is within the predetermined torso orientation range in the sleeping position. The predetermined torso orientation range is asymmetrical around a longitudinal y-axis of the person with respect to a vertical plane y-z to train the person to sleep on his right side or left side. For example, the predetermined torso orientation range is such that, in an x-z plane perpendicular to a longitudinal axis of the torso of the person in a supine position in a y-direction, the first stimulus is provided for a larger part of an upper right quadrant of the x-z plane then for an upper left quadrant of the x-z plane when viewed in a direction along the longitudinal axis from the torso to the feet of the person. In some embodiments, the first stimulus is provided for substantially the entire upper right quadrant of the x-z plane and the stimulus is not provided in at least a part of the upper left quadrant of the x-z plane, the quadrants being viewed in the y-direction along the longitudinal axis from the torso to the feet of the person (view from pillow side of the bed).

Another aspect of the present disclosure pertains to a method for reducing gastroesophageal reflux in a sleeping position of a person. In some embodiments, the method comprises affixing a stimulus generator to a torso of the person and using an orientation sensor to output a signal indicative of an orientation of the torso of the person. The stimulus generator is used to provide a first stimulus to the torso of the person to change the orientation of the torso of the person when the torso of the person is in a predetermined torso orientation range in a sleeping position. The method further involves receiving a first signal from the orientation sensor, the first signal being indicative of a first orientation of the torso of the person. The method may also involve determining on the basis of the first signal that the first orientation of the torso of the person is within the predetermined torso orientation range in the sleeping position. The predetermined torso orientation region is asymmetrical around a longitudinal y-axis of the person with respect to a vertical plane y-z to train the person to sleep on his right side or left side. For example, the predetermined torso orientation range is such that, in an x-z plane perpendicular to a longitudinal axis of the torso of the person in a supine position in a y-direction, the first stimulus is provided for a larger part of an upper right quadrant of the x-z plane then for an upper left quadrant of the x-z plane when viewed in a direction along the longitudinal axis from the torso to the feet of the person. In some embodiments, the first stimulus is provided for substantially the entire upper right quadrant of the x-z plane and the stimulus is not provided in at least a part of the upper left quadrant of the x-z plane, the quadrants being viewed in the y-direction along the longitudinal axis from the torso to the feet of the person (view from pillow side of the bed).

In some embodiments, the predetermined torso orientation range is such that the stimulus is not provided over an angle less than 30 degrees in the upper right quadrant of the x-z plane with respect to a z-axis of the x-z plane. This can allow the person P some flexibility in sleep position without being exposed to the stimulus signal to change sleeping position. In particular, some people desire to have the flexibility to sleep on their back or slightly towards their right side. The construction of the orientation range, particularly in the upper right quadrant XZ-1, is a trade-off between efficiently preventing or reducing reflux during sleep and sleep position flexibility (i.e. user comfort and, hence, a greater likelihood that the device is actually used).

In some embodiments, the orientation sensor is configured to measure the orientation of the torso of the person with a frequency having a range between 0.0001 Hz-0.1 Hz. For example, the range can be between 0.003 Hz-0.03 HZ, between 0.008 Hz-0.02 Hz, or approximately once per minute (approximately 0.017 Hz). In some embodiments, the orientation of the torso of the person is not measured during a stimulation period.

At least one of the parameters may be the same for the first and second stimulation period: a total energy of the stimulus, a maximum intensity of the stimulus. Further, the first and second stimulation period may be equally long.

The orientation sensor, stimulus generator and processing system may be physically separated, in which case in some embodiments, the orientation sensor, stimulus generator and processing system are configured to wirelessly communicate with each other. In some embodiments, there is a wired connection between the orientation sensor and the processing system and a wired connection between the processing system and the stimulus generator. Also, the orientation sensor, stimulus generator and processing system can be implemented within a single housing that can be affixed to the person.

In some embodiments, the sleep position training device comprises an adhesive surface for sticking the sleep position training device to the torso of the person. The adhesive surface may be the surface of a double-sided medical or silicon tape that has been applied to a surface of a housing of the sleep position training device. This embodiment eases the fixation of the sleep position training device to the torso of the person.

In some embodiments, the stimulus generator comprises a vibration generator and the stimulus is a vibrotactile stimulus to the chest of the person. This can make use of the high sensitivity of the chest to vibrotactile stimuli and thus can effectively provide the stimulus to the person. The intensity of the stimulus may be understood to be related to the amplitude of the vibration.

The presently disclosed training device and method enable to stimulate the person to substantially sleep on his left side and not on his right side (whereas this would be a suitable position to prevent or reduce snoring) and also not in a supine position. It has proven beneficial to sleep substantially on the left side to reduce gastroesophageal reflux during sleep.

It should be noted that the first stimulus, or any stimulus, need not to be applied directly to the person when the person is determined to be in the orientation range. Multiple determinations that the person is in the orientation range may occur before a stimulus is generated and/or applied to the person. For example, the processing system may determine the orientation of the person at (regular) time intervals and determine the orientation at a higher frequency once the person is determined to be in the orientation range for the first time. Only if a predetermined number of such more frequent determinations that the person is in the orientation range is made, the processing system may trigger the stimulus generator to generate the stimulus. This implementation avoids premature application of stimuli, e.g. when the person turns to a particular side for only a short time.

The sequence of the steps of receiving the first signal and determining that the torso of the person is in the predetermined torso orientation range may be repeated a plurality of times.

In some embodiments, the predetermined torso orientation range is such that the stimulus is also provided in a part of the upper left quadrant of the x-z plane and/or in at least a part of the lower right quadrant of the x-z plane. This embodiment extends the torso orientation range to other less favorable positions, such as a (near) supine position) wherein the stimulus is provided in order to train the person to assume an optimal sleeping position to reduce or avoid gastroesophageal reflux. The extension may be used for other indications as well, such as snoring.

In some embodiments, the predetermined torso orientation range is such that in an y-z plane, perpendicular to the x-z plane, the stimulus is not provided in at least a part of at least one of an upper left quadrant of the y-z plane and an upper right quadrant in the y-z plane. This embodiment enables flexibility to decide when the stimulus should be provided or not. For example, when the person is in certain positions in the y-z plane, e.g. in an upright position when the person gets out of bed or is reading, i.e. is awake, the stimulus should not be provided. For other situations, for example when the person uses several cushions, the stimulus should still be provided when the person is asleep.

In some embodiments, a sleep position training device can comprise an orientation means for affixing the device to the torso of the person in a correct orientation. Because the torso orientation range is asymmetrical around the y-axis, it may be beneficial to indicate to the user how the device should be positioned on the torso. The orientation means may comprise a visual indication, e.g. a graphical mark on the device or a light source located at one side of the device.

In some embodiments, a sleep position training device can include a processing system that is configured to trigger the stimulus generator to provide the stimulus when the torso of the person is in the predetermined torso orientation range only after a time duration. For example, the embodiment enables to the user to fall asleep without being bothered by stimuli from the device during the predetermined time duration. For example, the device may only start providing stimuli 20 minutes after the device has been switched on. In another example, the training device only provides stimuli when it appears that the person is asleep from data provided by the accelerometer.

In order to avoid that the person gets accustomed to particular stimuli and, therefore, is less likely to act on the stimuli, the present disclosure provides for a training device providing different subsequent stimuli each time the person is in the torso orientation range or each time the stimulus is applied (which may be several times when the person does not respond to stimuli).

In some embodiments, the sleep position training device receives a second signal from the orientation sensor, the second signal being indicative of a second orientation of the torso of the person, and determines on the basis of the second signal that the second orientation of the torso of the person is within the predetermined orientation range. Based on this determination, the stimulus generator provides a second stimulus that is different from the first stimulus. Again, the second stimulus signal does not need to be provided immediately after a first determination that the person is in the orientation range. In another embodiment of the disclosure the intensity of the first stimulus has a first time course during a first stimulation period, wherein the first time course is irregular. In particular, the intensity of the second stimulus has a second time-course during a second stimulation period and wherein the second time-course differs from the first time-course, wherein, optionally, the second time course is irregular. The first and second orientation of the torso may or may not be the same. Further, the second stimulation period may occur prior to or after the first stimulation period.

The disclosed sleep position training device according to these embodiments can prevent a person from getting used to a stimulus, which is undesirable because then the person would be less inclined to change the torso orientation and would thus more likely suffer from gastroesophageal reflux during sleep. The position training would thus become less effective. To reduce this problem, the time-course of the intensity of the stimulus during the first stimulation period can be different from the time-course of the intensity of the stimulus during another, previous or following, stimulation period. A time-course of the stimulus intensity may also be referred to as a stimulation pattern. In some embodiments, the sleep position training device can provide a stimulus having a different time-course during each stimulation period without having to change the total energy of the stimulus during the respective stimulation periods. By using irregular variations of the intensity, the possibilities for varying the time-courses increase. To illustrate, for a given total energy of the stimulus during a stimulation period, the number of possible distinct time-courses is far greater when irregular intensity variations are allowed than when only regular, such as periodic, intensity variations are allowed. Thus, the disclosed sleep position training device according to these embodiments does not require, for habituation prevention, to provide ever stronger stimuli of ever higher frequency. Herewith, the power consumption of the device is reduced.

Being able to vary the time-courses without having to change the total energy of the stimulus during a stimulation period is especially advantageous when the stimulus is provided to the upper part of the torso (the chest) of a person. The middle of the chest is a very suitable body part for providing a stimulus to because the breastbone (also called the sternum) is very sensitive, especially to vibrations, also called bone conduction, a technology also used in for loudspeakers worn on the head, placed on the bone behind the ear. To illustrate, vibrotactile stimuli to the breastbone can cause vibrations in the chest cavities of a person, which the person readily feels. However, because the breastbone is so sensitive, the total amount of energy of a stimulus during a stimulation period can only be varied within a limited range. Increasing the total stimulus energy above a threshold will namely wake the person. Since the breastbone is so sensitive, this threshold is relatively low and thus easily reached. Therefore, it can be useful to be able to prevent habituation to provided stimuli without having to increase the total stimulus energy. The sleep position training device can be used to prevent habituation to the stimulus, even when the stimulus is applied to the breastbone.

A time course of a quantity may be understood to be the variation of that quantity with time. Hence, the intensity of the stimulus having an irregular time-course during a stimulation period may be understood as that the intensity of the stimulus varies irregularly with time during the stimulation period. Optionally, causing the stimulus generator to provide the stimulus with irregularly varying intensity during a stimulation period comprises randomly varying the intensity of the stimulus during the stimulation period.

A determination that the orientation of the torso of the person is within the predetermined orientation range may be referred to as a trigger determination. A stimulation period may be understood to be triggered by such trigger determination, but is not required to start immediately after the trigger determination as described above and may require a predetermined number of more frequent trigger determinations before the stimulation period is started. A stimulation period is the period during which stimulus signals can be generated, which may be a fixed period of e.g. less than 10 seconds, e.g. 5 seconds or 4 seconds. More in particular, a stimulation period may be understood to be a predetermined period that starts at a first time instance after a predetermined number of trigger determinations and ends at a second time instance after the trigger determination. The first and second time instances may be predetermined and the second time instance typically is before the moment that the orientation of the torso is assessed again in the normal, lower frequency, sequence of torso orientation range assessments. The first time instance may be the moment that the trigger determination is made. Additionally or alternatively, a stimulation period for a particular trigger determination may be understood to begin at the moment that the stimulus generator starts to provide the stimulus for the first time after the particular trigger determination has been made and may be understood to end at the moment the stimulus generator ceases to provide the stimulus until after a potential next trigger determination. Further, a stimulation period is typically caused by a single, but not necessarily the first, trigger determination.

In some embodiments, the second time-course is irregular. This provides even more possibilities for ensuring that the respective time courses of the stimulus intensity during the first and second stimulation period differ. Of course, the stimulus may be provided to the person during a plurality of respective stimulation periods and the time course of the intensity may be irregular during each of these stimulation periods.

In some embodiments, causing the stimulus generator to provide the stimulus during the first, and optionally second, stimulation period comprises causing the stimulus generator to switch between an on-state and off-state, wherein the stimulus generator in the on-state provides the stimulus having a nonzero intensity, e.g. having a substantially constant intensity, and in the off-state does not provide the stimulus or provides the stimulus having a substantially zero intensity. This embodiment enables a convenient manner for causing the intensity of the stimulus to vary irregularly, because the stimulus generator can be simply controlled to switch on and off irregularly. Optionally, this embodiment comprises causing the stimulus generator to switch from the off-state to the on-state at least twice during a stimulation period.

When in the on-state, the stimulus generator may provide the stimulus at a certain constant intensity. This constant intensity may be the same or different for different on-states.

In some embodiments, causing the stimulus generator to provide the stimulus during the first, and optionally second, stimulation period comprises causing the stimulus generator during the first, and optionally second, stimulation period to subsequently be in the on-state during a first subperiod, in the off-state during a second subperiod and in the on-state during a third subperiod, wherein the first subperiod is longer or shorter than the third subperiod. This embodiment provides a convenient manner for irregularly varying the intensity of the stimulus during a stimulation period.

In some embodiments, causing the stimulus generator to provide the stimulus during the first, and optionally second, stimulation period comprises causing the stimulus generator during the first, and optionally second, stimulation period to subsequently be in the on-state during a fourth subperiod, in the off-state during a fifth subperiod, in the on-state during a sixth subperiod, in the off-state during a seventh subperiod and in the on-state during an eighth subperiod, wherein the fifth subperiod is longer or shorter than the seventh subperiod. This embodiment provides a convenient manner for irregularly varying the intensity of the stimulus during a stimulation period.

In some embodiments, the processing system has stored a plurality of different time courses for the stimulus intensity during a stimulation period. In this embodiment, causing the stimulus generator to provide the stimulus during the first stimulation period comprises selecting, for example randomly selecting, a particular time course out of the plurality of time courses and causing the stimulus generator to provide the stimulus in accordance with the selected time course. Providing the stimulus during any stimulation period, such as the second stimulation period, may comprise selecting, for example randomly selecting, a time-course out of the plurality of time-courses. This embodiment enables to quickly cause the stimulation generator to provide an appropriate stimulus.

For sleep position training devices in general, the stimuli can be generated during light sleep stages of the sleep cycle when the person is in a predetermined orientation range. Such light sleep stages are known to occur several times during a sleep period and are sometimes referred to as N1 and N2 sleep stage. Other sleep stages that are distinguished are N3 (deep sleep stage), R is a REM sleep stage and W is awake.

One other aspect of the present disclosure pertains to a sleep training device that is configured to generate stimuli to a person using an accelerometer to determine the sleep stage of the person and to trigger application of the stimuli to the person in dependence of the determined sleep stage and the predetermined orientation range. The dependency on the sleep stage may e.g. be that the stimulus is applied to the person or not dependent on the sleep stage and/or that the type of stimulus is dependent on the sleep stage. In this manner, it is possible to apply stimuli to the person, e.g. to the torso, when the person is in a light sleep stage and in a predetermined orientation range. The accelerometer may be used for determining the orientation of the person and for detecting the sleep stage.

It should be noted that the sleep training device may, in addition to the signals from the accelerometer use further sleep stage information to determine light sleep stages. This information may include at least one of sleep stage sequence information (e.g. it is known that when a person goes to sleep, the person always goes through a light sleep stage (i.e. N1 and/or N2), before he or she enters a deep sleep stage and timing information (e.g. the approximate time duration of one or more of the sleep stages may be known). The information may be used in a decision algorithm performed in the sleep position training device to decide whether or not a stimulus signal should be provided.

It should be noted that this type of sleep stage determination can be used in any sleep position training device, irrespective of the indication (snoring, acid reflux, etc.) and irrespective of the applied orientation range (symmetric or asymmetric in any direction).

In particular, one aspect of the disclosure relates to a sleep position training device that is affixable to an upper part of the torso of a person, e.g. the breastbone (sternum) of the person. The sleep position training device comprises an accelerometer (e.g. a triaxial accelerometer) configured to output an acceleration signal indicating respiratory variations of the person. The accelerometer is in direct contact to the upper part of the torso of the person to facilitate sufficiently accurate acceleration measurement, e.g. by sticking the device to the breastbone of the person. The device also comprises a processing system configured for receiving the acceleration signal from the accelerometer and to derive a respiratory rate variability (RRV) for the person. Also, the device comprises a stimulus generator configured to provide a first stimulus to the person when the person is in a predetermined orientation range in a sleeping position, wherein the first stimulus is dependent on the respiratory rate variability derived by the processing system. Again, other information may be used in the decision algorithm to decide whether or not the stimulus signal should be provided.

Another aspect pertains to a method for training sleep position of a person, comprising affixing a stimulus generator to an upper part (chest) of the torso of a person, using an accelerometer to output an acceleration signal indicating respiratory variations of the person, deriving a respiratory rate variability from the acceleration signal and providing a stimulus to the person to change the orientation of the person when the person is in a predetermined orientation range in a sleeping position, wherein the first stimulus is dependent on the derived respiratory rate variability.

It should be appreciated that these aspects wherein RRV parameter(s) is/are used to determine the sleep stage of the person may or may not be applied for reducing gastroesophageal reflux by applying stimuli to the person in dependence of these RRV parameters. The same RRV data obtained by measuring acceleration signals from the person may be used for other indications, such as snoring, to determine a sleep state and apply stimuli during a particular sleep state and independence on an orientation range configured for that indication.

In particular, an embodiment of a sleep position training device and method comprises a processing system configured for comparing the derived respiratory rate variability with at least one variability threshold set to distinguish between a first sleep stage and a second sleep stage of the person, wherein the processing system is configured to trigger the stimulus generator to provide the first stimulus when the person is in the first sleep stage and to not trigger the stimulus generator to provide the first stimulus when the person is in the second sleep stage. The first sleep stage may be a light sleep stage during which the person is more responsive to the stimuli than during a deep(er) sleep stage. The first sleep stage may be a light sleep stage, e.g. an N1 or N2 stage, whereas the second sleep stage may be a N3, wake or REM stage.

In some embodiments, the sleep position training device comprises an accelerometer that is used both for determining the orientation of the person and for detecting the sleep stage of the person. This can save hardware for the device.

It should be noted that other ways of estimating the sleep stage of the person can be used.

One aspect of this disclosure relates to a computer program comprising instructions to cause the sleep position training device as described herein to perform one or more of the method steps as described herein.

One aspect of this disclosure relates to a non-transitory computer-readable storage medium having stored thereon this computer program.

As will be appreciated by one skilled in the art, aspects of the present disclosure may be embodied as a system, a method or a computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Functions described in this disclosure may be implemented as an algorithm executed by a processor/microprocessor of a computer. Furthermore, aspects of the present disclosure may take the form of a computer program product embodied in one or more computer readable medium(s) having computer readable program code embodied, e.g., stored, thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples of a computer readable storage medium may include, but are not limited to, the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of the present disclosure, a computer readable storage medium may be any tangible medium that can contain, or store, a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber, cable, RF, etc., or any suitable combination of the foregoing. Computer program code for carrying out operations for aspects of the present disclosure may be written in any combination of one or more programming languages, including an object oriented programming language such as Java™, Smalltalk, C++ or the like and conventional procedural programming languages, such as the "C" programming language or similar programming languages. The program code may execute entirely on the person's computer, partly on the person's computer, as a stand-alone software package, partly on the person's computer and partly on a remote computer, or entirely on the remote computer or server. In the latter scenario, the remote computer may be connected to the person's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems), and computer program products according to embodiments of the present disclosure. It will be understood that each block of the flowchart illustrations and/or block diagrams, and combinations of blocks in the flowchart illustrations and/or block diagrams, can be implemented by computer program instructions. These computer program instructions may be provided to a processor, in particular a microprocessor or a central processing unit (CPU), of a general purpose computer, special purpose computer, or other programmable data processing apparatus to produce a machine, such that the instructions, which execute via the processor of the computer, other programmable data processing apparatus, or other devices create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function (s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts, or combinations of special purpose hardware and computer instructions.

Moreover, a computer program for carrying out the methods described herein, as well as a non-transitory computer readable storage-medium storing the computer program are provided. A computer program may, for example, be downloaded (updated) to the existing sleep position training device or be stored upon manufacturing of the device.

Elements and aspects discussed for or in relation with a particular embodiment may be suitably combined with elements and aspects of other embodiments, unless explicitly stated otherwise. Embodiments of the present disclosure will be further illustrated with reference to the attached drawings, which schematically will show embodiments according to the disclosure. It will be understood that the present disclosure is not in any way restricted to these specific embodiments.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIGS. 3A-3H are schematic illustrations of a predetermined torso orientation range in accordance with disclosed embodiments;

FIG. 11 depicts a processing system according to an embodiment.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the presently disclosed embodiments. Embodiment examples are described as follows with reference to the figures. Identical, similar or identically acting elements in the various figures are identified with identical reference numbers and a repeated description of these elements is omitted in part to avoid redundancies.

Typically, during sleep position training, the sleep posture of a sleeping person is monitored and when it is determined that the sleeping person is in a snoring inducing position, feedback, such as a vibration, is provided to the person. In some embodiments, the feedback does not wake the person, yet is strong enough to irritate the person causing him to change his sleep posture.

Figure 1:
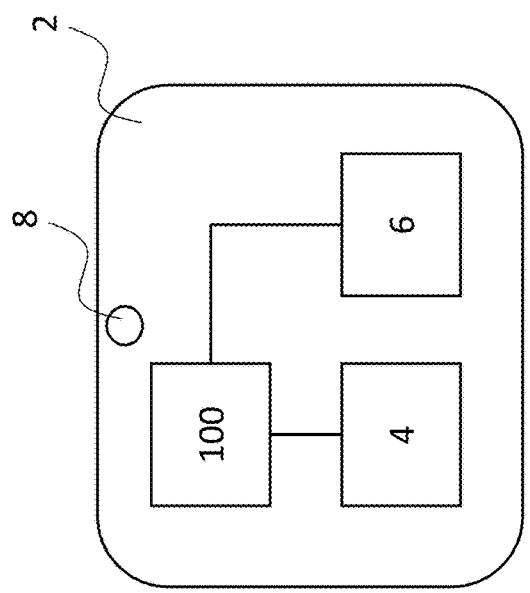
FIG. 1 schematically depicts a sleep position training device according to a disclosed embodiment.

FIG. 1 illustrates an embodiment of a sleep position training device 2. The device 2 comprises a processing system 100, an orientation sensor 4 and a stimulus generator 6. The processing system 100 may comprise a Printed Circuit Board (PCB) to which the orientation sensor 4 and stimulus generator 6 are connected. The processing system 100 may be understood to control the operation of the sleep position training device 2. The sleep position training device 2 may comprise orientation means 8 for correctly positioning the device on the person, e.g. a LED light that emits light when the device is activated. The device 2 may be affixed to the torso of the person.

In some embodiments, the orientation sensor 4 can be configured to output a signal indicative of an orientation of the torso of the person. In some embodiments, the orientation sensor comprises an accelerometer, such as a triaxial accelerometer. The accelerometer can be a MEMS (micro electro-mechanical systems) accelerometer as, for example, described in WO2007/061756 A2, which is incorporated herein in its entirety.

The stimulus generator 6 can be configured to provide a stimulus to the person for inducing the person to change his or her position. The stimulus generator 6 can comprise a vibration generator and the stimulus may be a vibrotactile stimulus to the body of the person, e.g. to the torso of the person, such as the chest of the person. In particular, the vibration generator may be a coin vibration motor, also called shaftless or pancake vibrator motors, generally having a diameter between 8 and 12 mm. Other types of stimuli include weak electrical currents or sound.

In some embodiments, the sleep position training device 2 may further comprise a power source (not shown) such as a non-rechargeable battery, for example a button cell, in particular a CR2032 cell (referring to the International standard IEC 60086-3).

Also, the sleep position training device 2 may comprise means for switching the device on and off (not shown) in response to a person interaction.

The sleep position training device 2 may be embodied as a single pad-like device comprising the orientation sensor 4, stimulus generator 6 and processing system 100. The size of the device can vary, but in one embodiment the pad device may have dimensions of approximately 4 cm by 4 cm by 1 cm. In one example, the sleep position training device 2 comprises an adhesive surface for sticking the sleep position training device 2 to the body of the person. Just before a person goes to sleep, he or she can apply double-sided medical tape to the pad and can stick the pad to his body, such as his chest.

The processing system 100 is configured to determine whether or not the orientation of the person's torso is outside a predetermined orientation range. The processing system 100 may therefore have stored the orientation range beforehand. Optionally, a person is able to set the orientation range before using the device 2. The orientation range may be understood to be the range in which there may be a significant health issue, such as snoring or (nocturnal) gastroesophageal reflux.

Figure 2:
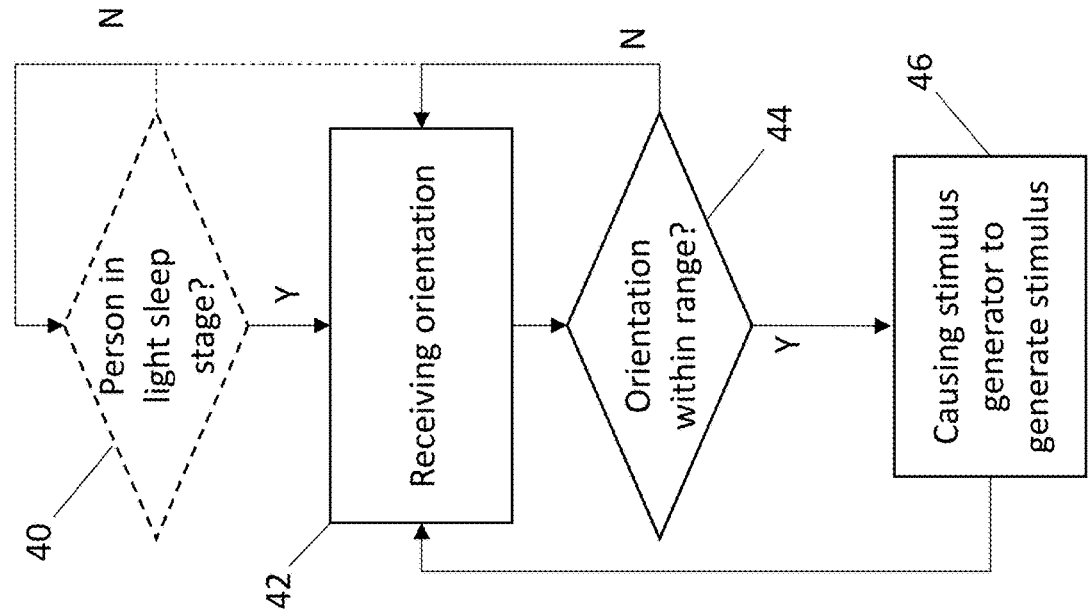
FIG. 2 depicts steps of a method performed by a sleep position training device in accordance with a disclosed embodiment.

FIG. 2 illustrates some steps of an embodiment of a method performed by the sleep position training device 2, more particularly the processing system 100.

As an optional step, the sleep position training device 2 may determine whether the person is in a light sleep stage in step 40. For sleep position training devices in general, the stimuli can be generated during light sleep stages of the sleep cycle when the person is in the predetermined orientation range. Such light sleep stages are known to occur several times during a sleep period and are sometimes referred to as N1 and N2 sleep stage as N3 is a deep sleep stage and R is a REM sleep stage and W is awake. During light sleep stages, the person is more susceptible to the stimuli and during deep sleep stages, the stimuli may not have effect or may wake up the person.

Various ways can be used for assessing the sleep stage of the person. In some embodiments, an accelerometer can be used to detect the sleep stage of the person, which may be (but not necessarily) the same entity as orientation sensor 4. The accelerometer 4 can be used to derive the respiratory rate variability of the person when the orientation sensor is directly applied to the chest, e.g. to the breastbone, of the person. This method will be described in more detail with reference to FIGS. 6A and 6B.

It should be noted that the determination of the sleep stage, if determined at all, may be performed at any point in time before the stimulus is generated.

Going back to FIG. 2, as a next step, the processing system 100 receives a signal from orientation sensor 4 indicating the orientation of the person in step 42 and determines whether or not the orientation of the person is in the orientation range in step 44. If not, the processing system 100 continues to determine the orientation of the person and, optionally, the sleep stage.

If the orientation of the person is within the orientation range, stimulus generator 6 may be triggered to cause generation of a stimulus in step 46 that is applied to the body of the person. The stimulus may be a single vibration or a set of vibrations as will be described in more detail below.

The processing system may determine the orientation of the person at (regular) time intervals and determine the orientation at a higher frequency once the person is determined to be in the orientation range for the first time. Only if a predetermined number of such more frequent determinations that the person is in the orientation range is made, the processing system may trigger the stimulus generator to generate the stimulus. This implementation avoids premature application of stimuli, e.g. when the person turns to a particular side for only a short time. The regular time interval at which orientations are determined may e.g. be 1 minute and, if the person is determined to be in the orientation zone, further orientations may be determined a number of times within that minute, e.g. every 4 seconds. Only when a number of such more frequent determinations results in a finding that the person is in the orientation zone, the stimulus may be applied.

The orientation range applied by the processing system 100 may be defined as a range of orientation angles.

In some embodiments, the processing system 100 applies a predetermined torso orientation region that is asymmetrical around a longitudinal axis of the person to train the person to sleep on his right side or left side.

FIGS. 3A-3H are schematic illustrations of how a predetermined torso orientation range O can be viewed using a scheme with perpendicular axes, sometimes referred to as a Cartesian coordinate scheme. It should be appreciated that other representations, like polar schemes or alternative schemes can be derived to the same scheme as FIGS. 3A-3E by a suitable set of transformations and rotations.

Figure 3B:
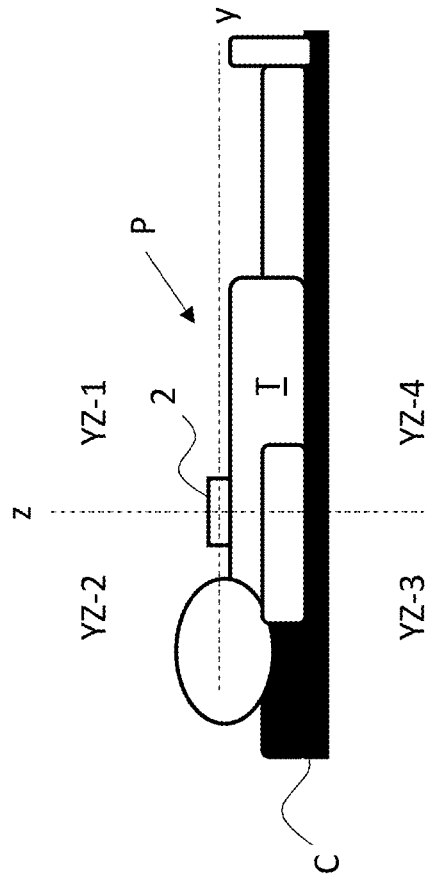
Figure 3A:
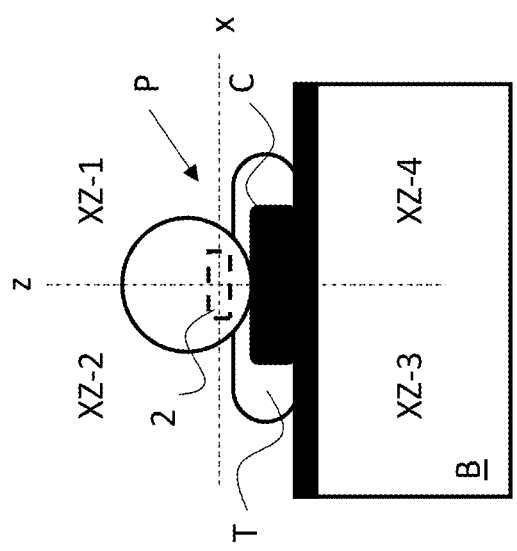

FIGS. 3A and 3B are schematic views of a person P in resp. an x-z plane and a y-z plane resting on a bed B using a cushion C to support the head. The sleep position training device 2 is drawn to be attached to the torso T of the person P and is considered to be in the origin of both the x-z plane and the y-z plane. Quadrants of the x-z and y-z planes are bounded by the half-axes and indicated as XZ-1 to XZ-4 resp. YZ-1 to YZ-4 according to the convention for Cartesian schemes.

In some embodiments, the sleep position training device 2 can be configured to stimulate the person to substantially sleep on his left side and not on his right side or on the back (supine position). It has proven beneficial to sleep substantially on the left side to reduce gastroesophageal reflux during sleep. To that end, the predetermined torso orientation range O is such that, in the x-z plane perpendicular to a longitudinal axis of the torso T of the person P in a supine position in a y-direction, the stimulus is provided for a larger part of an upper right quadrant XZ-1 of the x-z plane than for an upper left quadrant XZ-2 of the x-z plane when viewed in a direction along the longitudinal y-axis from the torso T to the feet of the person P as illustrated in FIGS. 3C and 3D. In some embodiments, the first stimulus is provided for substantially the entire upper right quadrant of the x-z plane and the stimulus is not provided in at least a part of the upper left quadrant of the x-z plane as also illustrated in FIGS. 3C and 3D. As consequence of the torso orientation range defined in this manner, stimuli will primarily be applied to the person P when his torso is oriented towards the upper right quadrant XZ-1 as will be described in further detail with reference to FIGS. 4A and 4B.

In order to also trigger the stimulus for other less favorable orientations of the torso, the predetermined torso orientation range O is extended into the upper left quadrant XZ-2 and the lower right quadrant XZ-4 in order to train the person P to assume an optimal sleeping position to reduce or avoid gastroesophageal reflux during sleep. Extension into the upper left quadrant XZ-2 may be advantageous to avoid or reduce both gastroesophageal reflux and snoring, since snoring is most likely to be reduced when is not in a supine position.

Figure 3E:
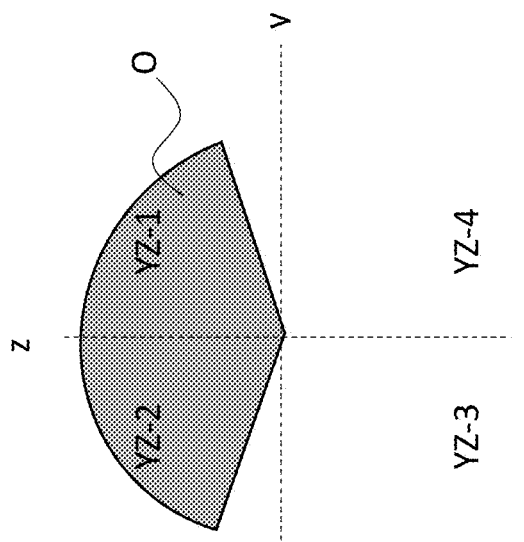
Figure 3D:
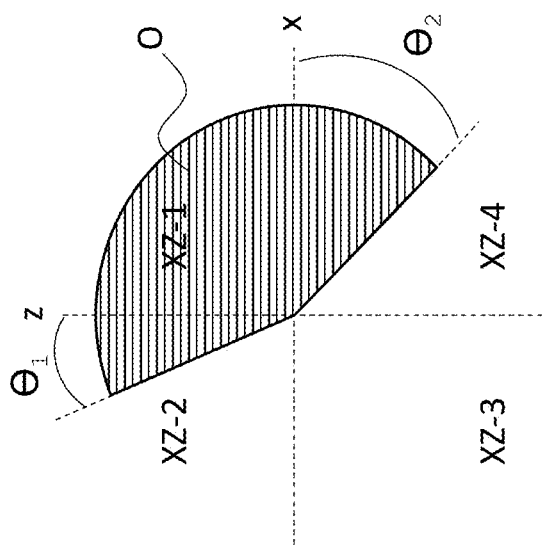
Figure 3C:
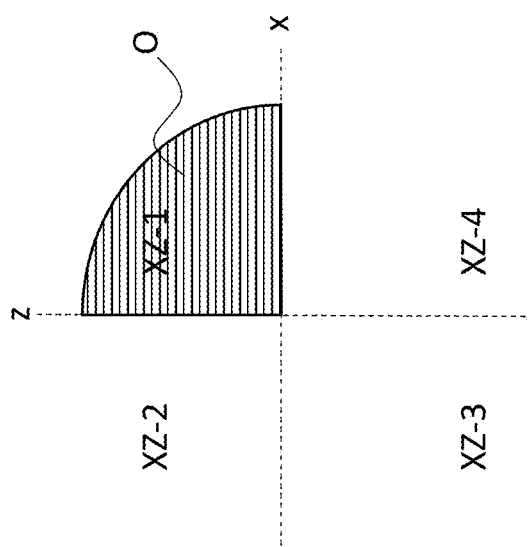

In FIG. 3E, it is shown that the torso orientation range O may, in addition, be defined in the y-z plane such that the stimulus is not provided in at least a part of at least one of the upper left quadrant YZ-2 of the y-z plane and the upper right quadrant YZ-1 in the y-z plane. This enables flexibility to decide when the stimulus should be provided or not in this direction. For example, when the person P is in certain positions in the y-z plane, e.g. in an upright position when the person gets out of bed or is reading, i.e. is awake, the stimulus should not be provided. For other situations, for example when the person uses several cushions C, the stimulus should still be provided when the person is asleep.

In some embodiments, as shown in FIG. 3D, the torso orientation range covers the entire upper right quadrant XZ-1 of the x-z plane and extends into the XZ-2 quadrant with an angle $\Theta_1$ of 45 degrees or less, e.g. 30 degrees or 20 degrees. The torso orientation range may also extend into the XZ-4 quadrant with an angle $\Theta_2$ of 90 degrees or less, e.g. 70 degrees, 45 degrees or 20 degrees. For the y-z plane, other angles may apply, such as an angle of 75 degrees or less on one or both sides of the z axis.

In three dimensions, the torso orientation range forms a pyramid with the apex located in or nearby the sleep position training device 2.

In some embodiments, the predetermined torso orientation range O covers the upper right quadrant XZ-1 substantially entirely, but not completely. An advantage of this embodiment is that the person P is allowed some flexibility in sleep position without being exposed to the stimulus signal to change sleeping position. In particular, some people desire to have the flexibility to sleep on their back or slightly towards their right side. The construction of the orientation range, particularly in the upper right quadrant XZ-1, is a trade-off between efficiently preventing or reducing reflux during sleep and sleep position flexibility (i.e. user comfort and, hence, a greater likelihood that the device is actually used).

FIGS. 3F-3H provide various embodiments wherein the orientation range O covers a substantial part of the upper right quadrant XZ-1.

In FIG. 3F, it is shown that the predetermined orientation range O covers a substantial part of the upper right quadrant XZ-1. The angle $\Theta_{3a}$ with the positive x-axis may e.g. be larger than 60 degrees, e.g. 70 degrees, such that angle $\Theta_{3b}$ is 30 degrees or even 20 degrees. Accordingly, a person P lying in the supine position or even slightly oriented to his right side will not receive a stimulus signal.

FIGS. 3G and 3H show that the predetermined orientation range O covers the complete. resp. a substantial part of the lower right quadrant XZ-4. Hence, the person P should also not lie on his belly with too much orientation to his right side. In FIG. 3H, the predetermined orientation range is substantially symmetrical with respect to the x-axis in the x-z plane. In some embodiments, angles $\Theta_{3a}$ and $\Theta_4$ are larger than 60 degrees, e.g. 70 degrees or higher.

Figure 4A:
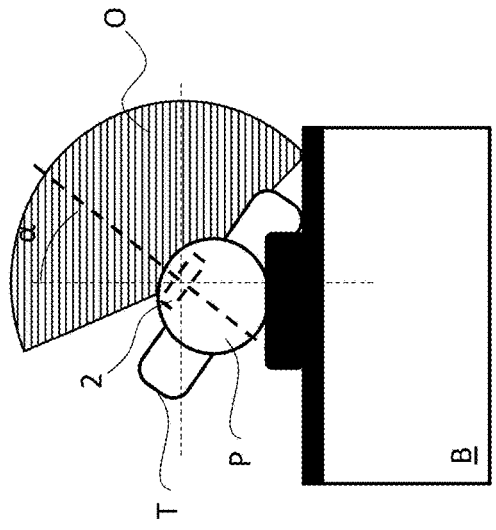
FIGS. 4A-4D are schematic illustrations of the sleep position training device in operation.
Figure 4B:
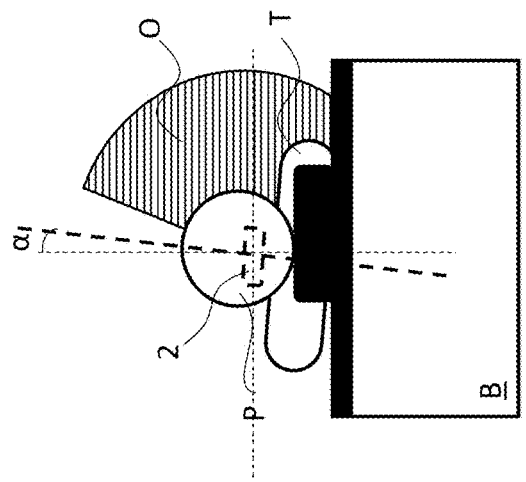

FIGS. 4A and 4B are illustrations of the operation of the sleep position training device 2 using the predetermined orientation range from FIG. 3D.

FIG. 4A shows the situation wherein a person has turned his torso T to the left. As shown, the orientation of the torso T makes an angle α which is determined from the signal of the orientation sensor 4 of the sleep position training device 2 with the z-axis and is outside of the predetermined torso orientation range O as determined by the processing system 2. Hence, for this particular application of reducing gastroesophageal reflux, the processing system 100 will not trigger the stimulus generator 6 to generate a stimulus signal since the person P is primarily on his left side.

When, during the sleep, the person P turns, as shown in FIG. 4B, the processing system 100 will detect from the signal of the orientation sensor 4 that the angle α has changed and is now in the predetermined torso orientation range O. Accordingly, the processing system 100 triggers the stimulus generator 6 to generate the stimulus signal and apply this to the torso T of the person P to induce the person P to change his orientation to his left side and, consequently, to reduce the change that reflux occurs. As mentioned above, in one particular application, the processing system 100 will take account of the sleep stage of person P such that device 2 will only generate the stimulus signal in a light(er) sleep stage of the person P.

Figure 4C:
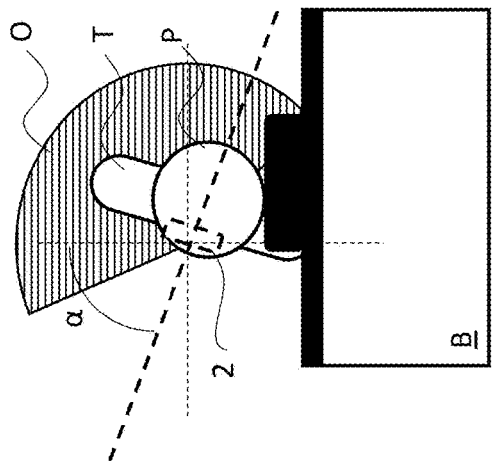
Figure 4D:
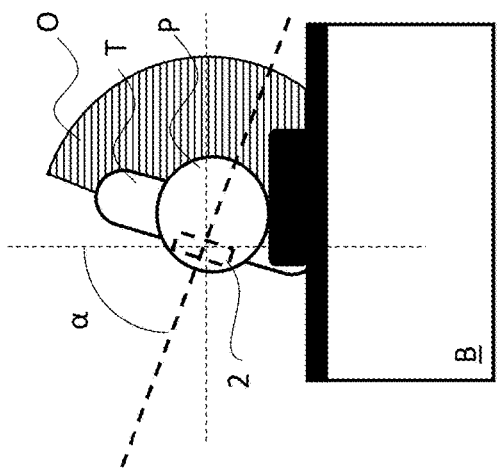

FIGS. 4C and 4D are illustrations of the operation of the sleep position training device 2 using the predetermined orientation range from FIG. 3H.

In FIG. 4C, similar to FIG. 4A, person P has turned torso T to the left and the stimulus generator 6 will not generate a stimulus signal because of this orientation.

In FIG. 4D, person P lies on his back with his torso slightly turned to his right side. Whereas for the torso orientation range) of FIG. 4B, this orientation would result in generating a stimulus signal, the reduced orientation range in the upper right quadrant of FIG. 3H prevents generation of a stimulus signal in this orientation. The angle from the z-axis over which person P may turn into the upper right quadrant may e.g. be 20 degrees. Alternatively, processing system 2 may start a timer and delay generation of a stimulus signal for a certain period of time. This period may be set or preset. When person P turns his body more to the right sight (not shown in FIG. 4D), angle α will enter the predetermined orientation range O and a stimulus signal will be generated stimulating the person to change his orientation to a position where reflux is less likely to occur.

Figure 5:
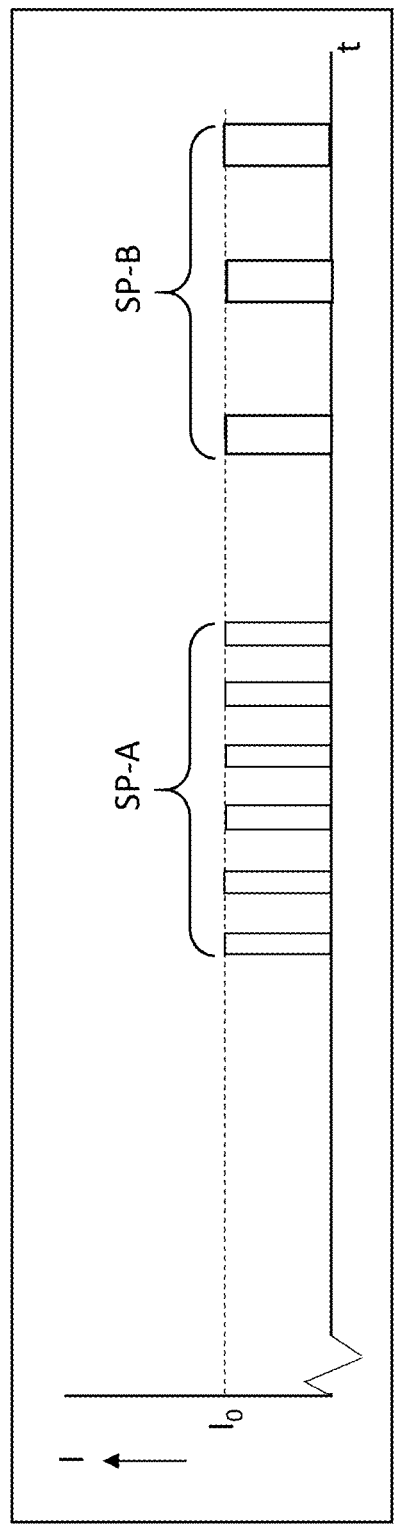
FIG. 5 shows different stimulus patterns generated by the sleep position training device.

FIG. 5 is a schematic illustration of an example of a stimulus signal provided as pulses during stimulation periods SP-A and SP-B when the person is in a predetermined orientation range and, optionally, when the person is in a light(er) sleep stage. The device 2 may be configured such that stimulus signals are not provided during an initial time period to allow the person to fall asleep in any orientation that he or she desires.

The stimulus signal can vary between stimulation periods. In some embodiments, the stimulus signal may be substantially identical for successive stimulation periods during which a stimulus signal is generated. In some embodiments, the stimulus signals can be different for successive stimulation periods and may be selected randomly from a plurality of stimulus signals.

In FIG. 5, the stimulation periods SP-A and SP-B are the same, e.g. smaller than 10 seconds. During a stimulation period SP, successive pulses can be applied. The number of successive vibration periods may vary between different stimulation periods, e.g. between 0 and 10 pulses, e.g. between 3 and 8 pulses. The time intervals between the vibration periods and the time duration of the of these periods may be varied and may be selected such that the total amount of energy for successive stimulation periods is substantially the same. In one embodiment, the total duration of the stimuli within the stimulation period may be the same. For example, in FIG. 5, stimulation period SP-A contains 6 vibration periods of a predetermined equal duration and stimulation period SP-B contains 3 vibration periods that each have a twofold duration of the vibration periods in SP-A.

In some embodiments, the minimum time interval between the vibration periods is 100 milliseconds (ms) and the maximum time interval is 400 ms. The minimum duration of a vibration period may be 500 ms and the maximum duration may be 3 seconds. For example, for a particular stimulation period, the aggregated duration of the stimuli is 4 seconds. For example, the first stimulation period may have 3 vibration periods: $1^{st}$=500 ms, interval 200 ms, $2^{nd}$=500 ms, interval 300 ms, $3^{rd}$=3 seconds. Another example of a stimulation period comprises 8 vibration periods: 1st=500 ms, interval 200 ms, $2^{nd}$=500 ms, interval 400 ms, $3^{rd}$=500 ms, interval 300 ms, $4^{th}$=500 ms, interval 200 ms, $5^{th}$=500 ms, interval 300 ms, $6^{th}$=500 ms, interval 400 ms, $7^{th}$=500 ms, interval 200 ms, $8^{th}$=500 ms.

It should be noted that stimulus signals may be different to avoid that the person gets used to the stimulus and is less like to respond. Examples of such different stimulus signals are described below with reference to FIGS. 8 and 9.

Figure 6A:
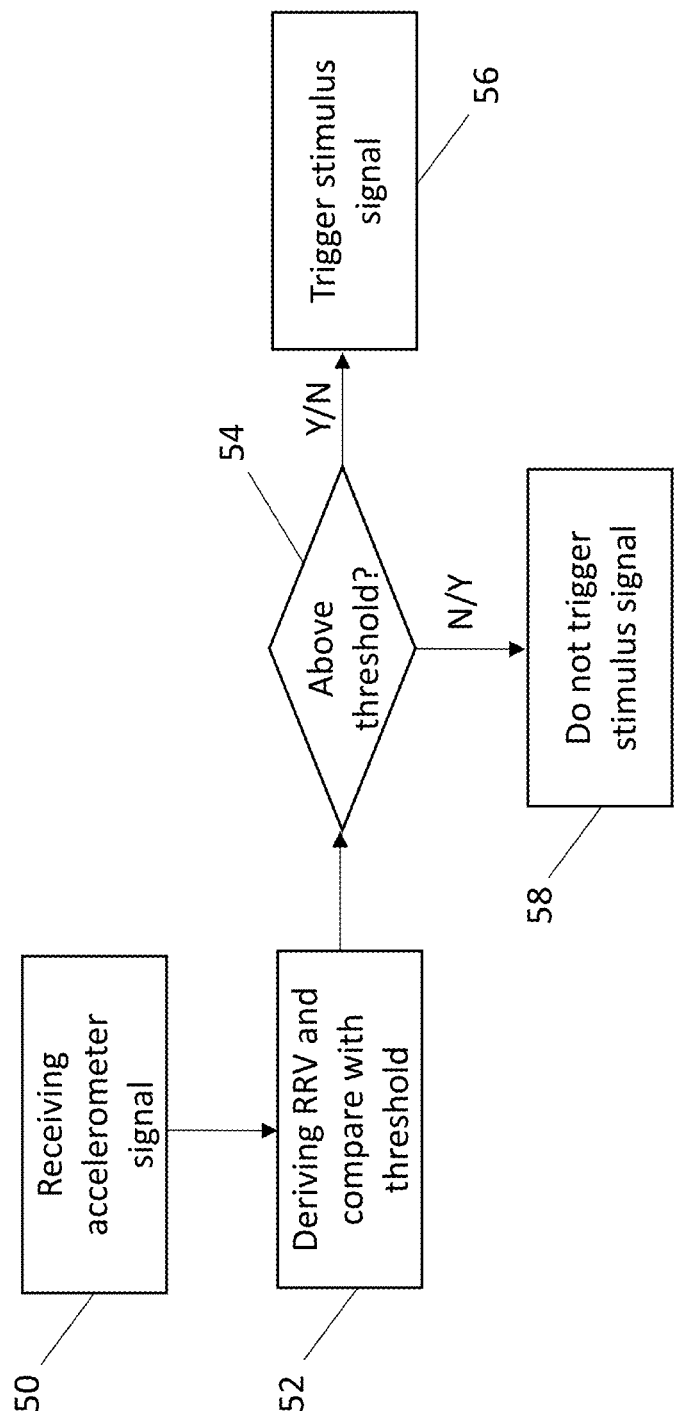
FIG. 6A shows steps of obtaining sleep stage information for a sleep position training device in accordance with a disclosed embodiment.

FIG. 6A is an illustration of some steps of a method in a sleep position training device to determine whether or not a stimulus signals should be provided to a person. It is noted that this device may apply any orientation range suitable for one or more indications, such as snoring and/or gastroesophageal reflux. In case of snoring, the orientation range is such that the person is not in a supine position causing the head to also being in a straight position (eyes facing the ceiling). If the head and body are in a supine position, the tongue falls in the airway more often because of gravity than when the person's head is tilted sideways or the person sleeps on his side. When the tongue is in the airway, it partially blocks the airway, which is an important cause of snoring. For the gastroesophageal reflux indication, the orientation range may be such as illustrated in FIGS. 3A-3E and FIGS. 4A-4B.

The sleep training device 2 of FIG. 1 may be configured to generate stimuli to a person using an accelerometer 4 to determine the sleep stage of the person and to determine the orientation of the person. In this manner, it is possible to apply stimuli to the person, e.g. to torso, when the person is in a light sleep stage and in a predetermined orientation range.

Figure 6B:
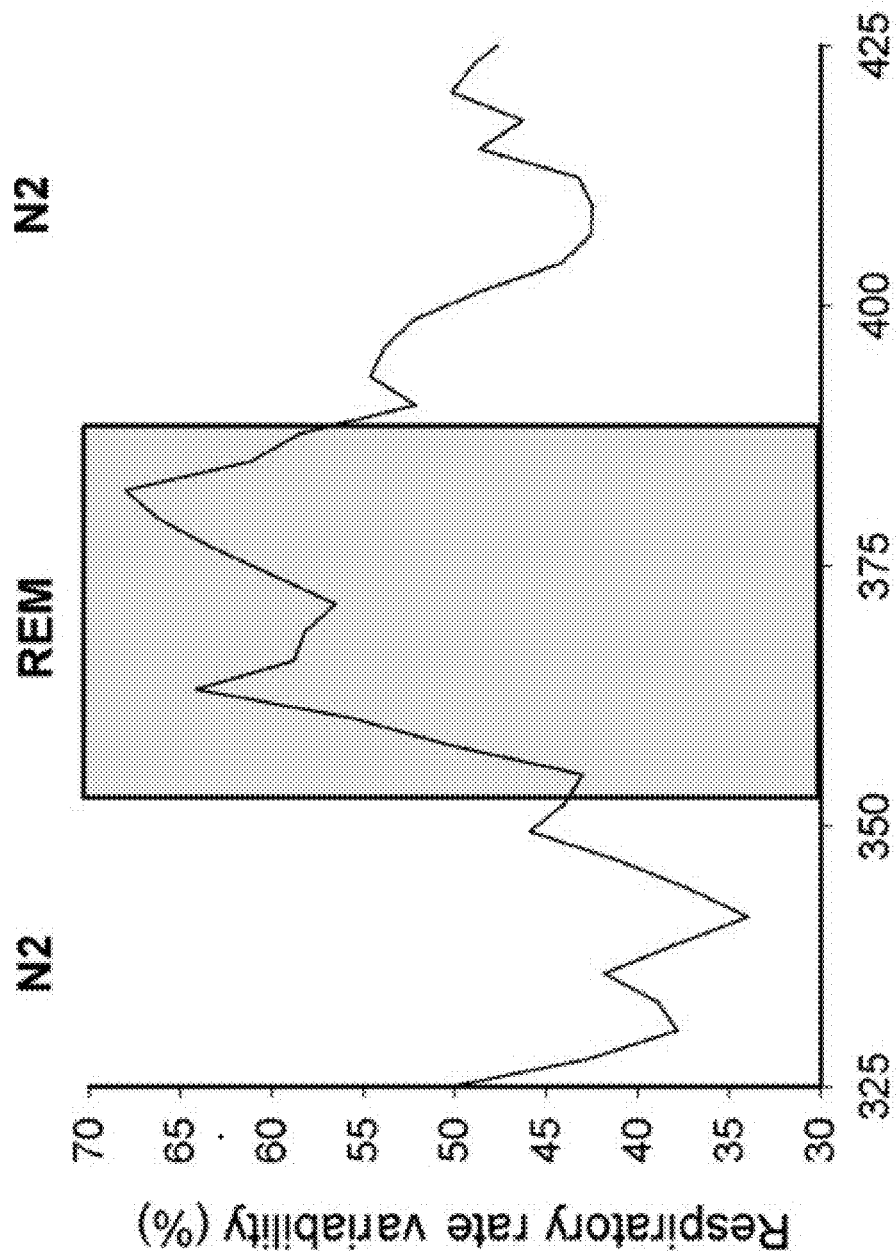
FIG. 6B shows an example of an RRV measurement in distinct sleep stages.

In some embodiments, the sleep position training device 2 is affixable to an upper part of the torso of a person, e.g. the chest of the person, such as the breastbone. The sleep position training device 2 comprises an accelerometer 4 (e.g. a triaxial accelerometer) configured to output an acceleration signal indicating respiratory variations of the person. The accelerometer 4 is in direct contact to the upper part of the torso of the person to facilitate sufficiently accurate acceleration measurements, e.g. by sticking the device directly on the breastbone of the person using a sticker. The sleep position training device 2 also comprises a processing system 100 configured for receiving the acceleration signals from the accelerometer 4 as shown in step 50 of FIG. 6A and to derive a respiratory rate variability (RRV) for the person as shown in the second step of FIG. 6A. The RRV can be used to detect the sleep stage of the person, as shown in FIG. 6B.

In some embodiments, the device 2 comprises a stimulus generator 6 configured to provide a first stimulus to the person when the person is in a predetermined orientation range (possibly only after a predetermined number of positive determinations as described above) in a sleeping position, wherein the first stimulus is dependent on the respiratory rate variability derived by the processing system.

In steps 52 and 54, shown in FIG. 6A, the processing system 100 is configured for comparing the derived respiratory rate variability with at least one variability threshold set to distinguish between at least a first sleep stage and a (consecutive) sleep stage. The processing system 100 is configured to trigger the stimulus generator 6 to provide the first stimulus (step 56) when the person is in the first (light) sleep stage and to not trigger the stimulus generator 6 to provide the first stimulus (step 58) when the person is in a deep, wake or REM sleep stage. The first sleeping stage may be a light sleep stage during which the person is more responsive to the stimuli than during a deep or REM sleep stage. The first (light) sleep stage may be a light sleep stage. an N1, N2, whereas the consecutive sleep stage may be a wake, deep or REM stage.

The respiratory rate variability (RRV) can be obtained by processing the acceleration signal from the accelerometer 4 and derive the RRV from the acceleration signals (e.g. using the formula RRV=100−measured acceleration/DC component %). A normal person breathes about 10-15 times per minute during sleep. The RRV may be determined for particular time intervals during the sleep of the person, e.g. during time intervals of 1 minute. The RRV may be obtained by applying a sliding time window and use a number of determined RRVs for successive time intervals before a decision on the sleep stage is made. Furthermore, the time windows of e.g. 1 minute may be applied to obtain an average respiration rate for each time window and the variability of the respiration rate by analyzing the variations for a number of time windows, e.g. 10, 5 or 3 time windows can be used. The RRV of RRV's can be compared to a threshold RRV value set to determine a sleep stage. For example, if the RRV is 50% or higher, or 55% or higher, the sleep stage may be determined to be a REM stage and no stimulus signal is generated. If the RRV is determined to be lower that the threshold, indicating lighter sleep stages, the stimulus signal is generated.

For example, if the RRV=38% for the first minute, 39% for the second minute, and 35% for the third minute, the sleep stage may be determined to be a light sleep stage and a stimulus signal can be triggered when the person is also in the predetermined orientation range.

In another example, if RRV=36% for the first minute, 37% for the second minute, 39% for the third minute, 60% for the fourth minute, 40% for the fifth minute, 38% for the sixth minute, 37% for the seventh minute and 39% for the eighth minute, the sleep stage will still be determined to be a light sleep stage. The fourth minute is likely to be an arousal. Only, if at least two successive time intervals after the fourth minute would also yield an RRV>50%, a determination would be made that the light sleep stage has passed and not stimuli should be applied to the person even if he is determined to be in the orientation range.

FIG. 6A is a part of a decision algorithm to detect on the sleep stage of a person using an accelerometer to derive the RRV for a sleep position training device and decide whether or not a stimulus should be applied to the person of the person in the predetermined orientation range. It should be noted that further information in addition to the RRV can be used in the decision algorithm. This information may include sleep stage sequence information (e.g. it is known that when a person goes to sleep, the person always goes through a light sleep stage (i.e. N1 and/or N2), before he or she enters a deep sleep stage. Other information includes timing information, e.g. the approximate time duration of one or more of the sleep stages may be known. A typical sleep stage is known to last e.g. 20 minutes and this information can be used in connection with the RRV determinations to decide whether the stimulus should be provided. The algorithm may decide to not trigger the stimulus to be applied near the expected transition boundary from the light sleep period to a deeper sleep period even when the determined RRV still indicates a light sleep stage.

Figure 7B:
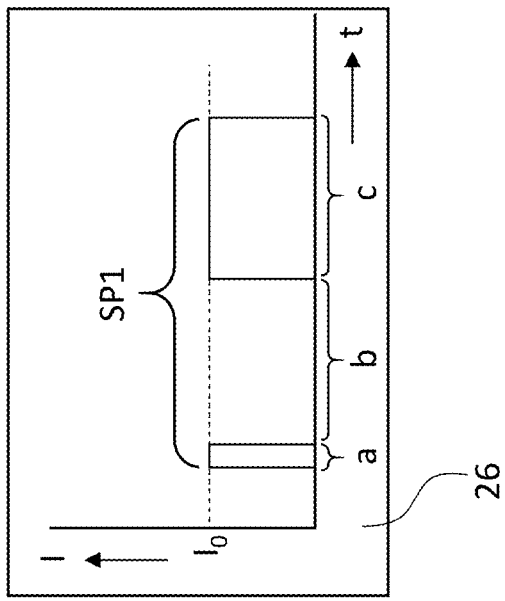
FIGS. 7A, 7B, and 7C illustrates steps of a method according to a different embodiment.
Figure 7C:
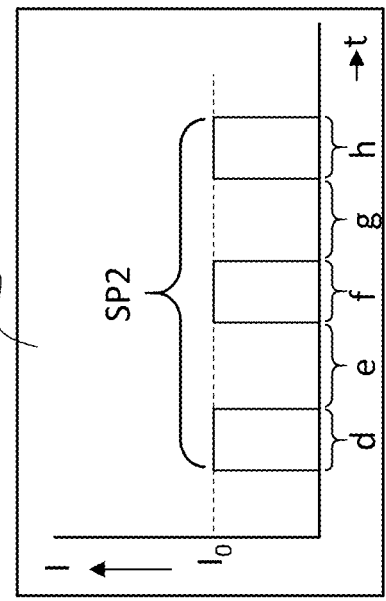
Figure 7A:
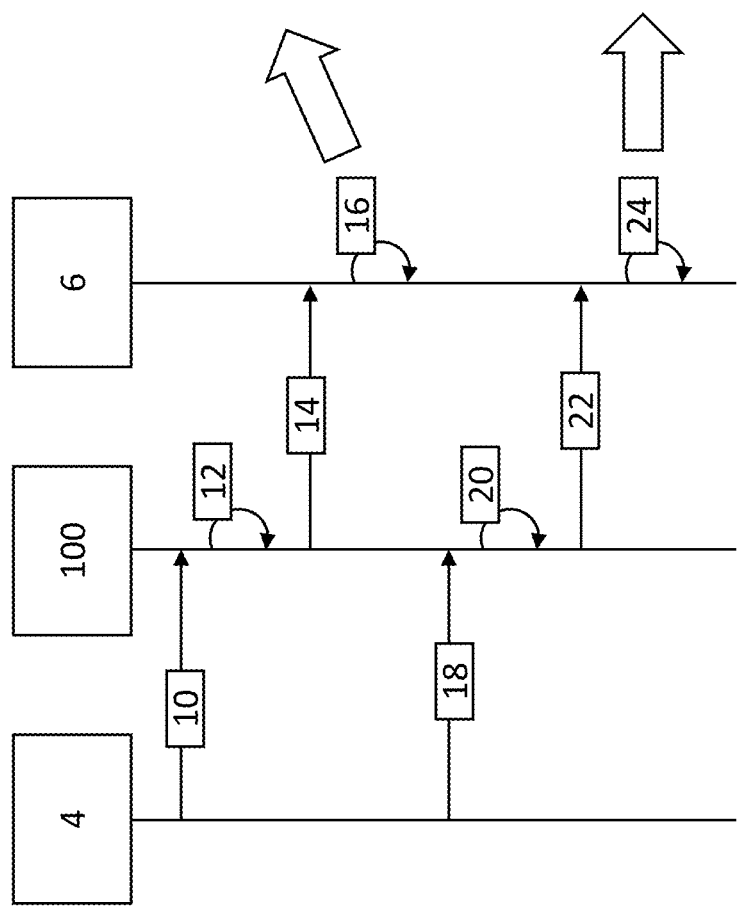

FIGS. 7A-7C illustrates steps that are performed during operation of the device 2 according to one embodiment. In step 10, the orientation sensor 4 outputs a signal indicative of the orientation of the torso T of the person P. The orientation sensor 4 may feed this signal to the processing system 100. The processing system 100 receives the signal and determines, based on this signal, in step 12 that the orientation of the person's torso is within the predetermined orientation range O.

Based on this determination or determinations if multiple determinations are required, the processing system 100, in step 14, causes the stimulus generator 6 to provide the stimulus to the person during a first stimulation period SP1 for inducing the person to change the orientation of his torso/body. In some embodiments, the stimulus is provided to one location on the breastbone. The processing system 100 may transmit a control signal in step 14 that causes the stimulus generator to act. Window 26 shows the time-course of the stimulus intensity during the first stimulation period SP1. The time-course is irregular. The stimulation period comprises three subsequent sub-periods a-c. The stimulus generator 6 switches between an on-state and an off-state. In sub-periods a and c, the stimulus generator 6 is in the on-state and thus provides the stimulus with nonzero intensity, in particular with a constant intensity $I_0$ as indicated. In sub-period b, the stimulus generator is in the off-state and does not provide the stimulus. The intensity in stimulation period SP1 varies irregularly in the sense that the on-state sub-periods, a and c, are not equally long.

Stimulus intensity may indicate the power of the stimulus, for example the vibrational power. Therefore, the surface area below the intensity-time graph, i.e. the surface area of the three block pulses, may indicate the total energy of the stimulus during the stimulation period.

FIG. 7 further shows optional steps 18-24. In step 18, the orientation sensor 4 outputs another signal indicative of the orientation of the torso. The processing system 100 receives this signal and, based on this signal, determines in step 20 again that the orientation of the person is within the predetermined orientation range O. Based on this determination (or multiple determinations), in step 22, the processing system causes the stimulus generator to provide the stimulus during a second stimulation period SP2. The stimulus generator 6 provides this stimulus in step 24. As shown in window 28, the time-course of the stimulus intensity during the stimulation period SP1 differs from the time-course of the stimulus intensity during the stimulation period SP2. Further, the time-course of the intensity of the stimulus is regular for stimulation period SP2. The sub-periods d, f and h are namely equally long and furthermore separated by sub-periods e and g that are also equally long.

FIG. 8 illustrates how the time-course of a stimulus intensity can be different for different stimulation periods in case the stimulus intensity is to vary regularly during the stimulation periods. In FIGS. 8A-8D, the vertical axis denotes the intensity of the stimulus, the horizontal axis denotes time. The respective stimulation periods are indicated by SP1, SP2, SP3 and SP4. FIG. 8A shows a reference time-course of a stimulus intensity during a stimulation period SP1. Stimulation period SP1 contains three sub-periods wherein the intensity of the stimulus has a value of $I_0$ and two intermediate sub-periods wherein no stimulus is provided.

Figure 8A:
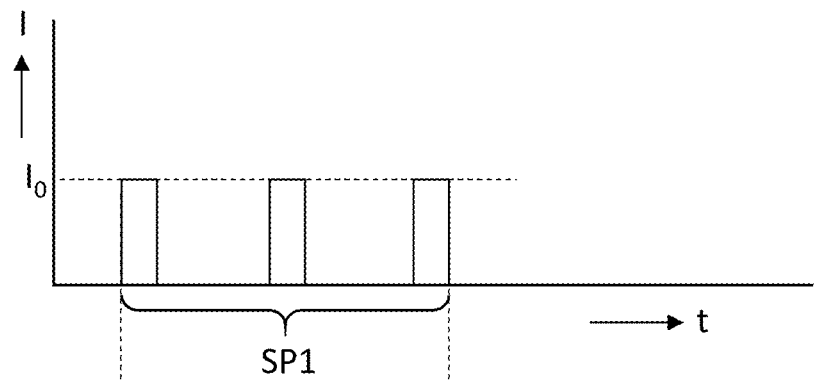
FIGS. 8A, 8B, 8C, and 8D show regular time-courses for a stimulus intensity.
Figure 8B:
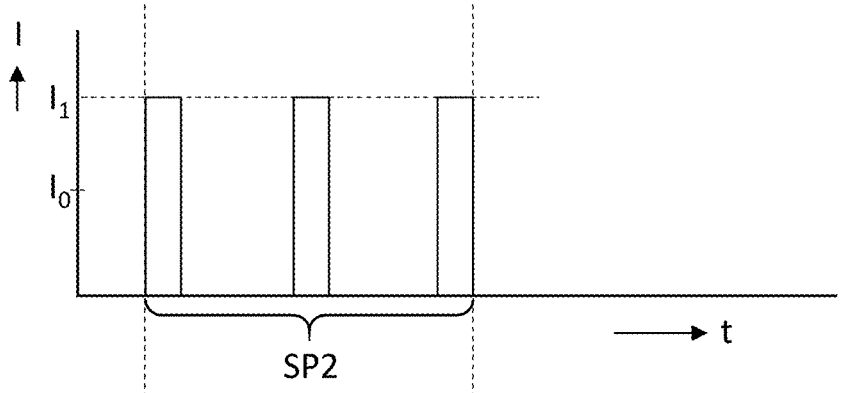

FIG. 8B shows a time-course of the intensity for a stimulation period SP2. The time-course of the intensity of FIG. 8B differs from the time-course of FIG. 8A in that the stimulus, if provided, has a higher intensity Ii. Further, the frequency is the same as well as the duration of the stimulation period.

Figure 8C:
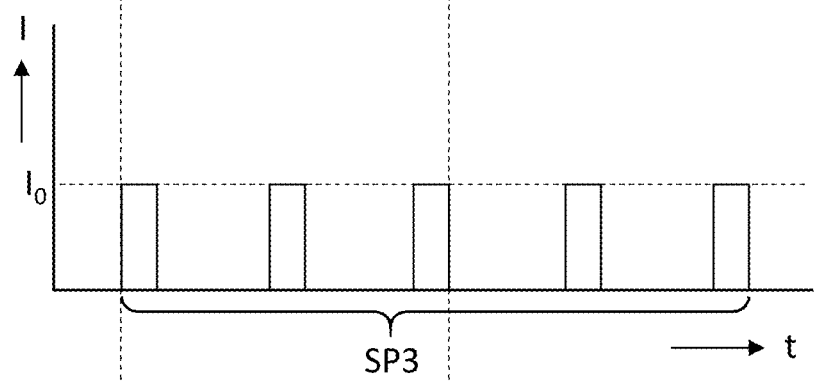

FIG. 8C shows a time-course of the intensity for a stimulation period SP3. This time-course differs from the time-course of FIG. 8A in that the stimulation period SP3 is longer than SP1. However, the intensity with which the stimulus is provided is the same $I_0$ as well as the frequency with which the stimulus is provided.

Figure 8D:
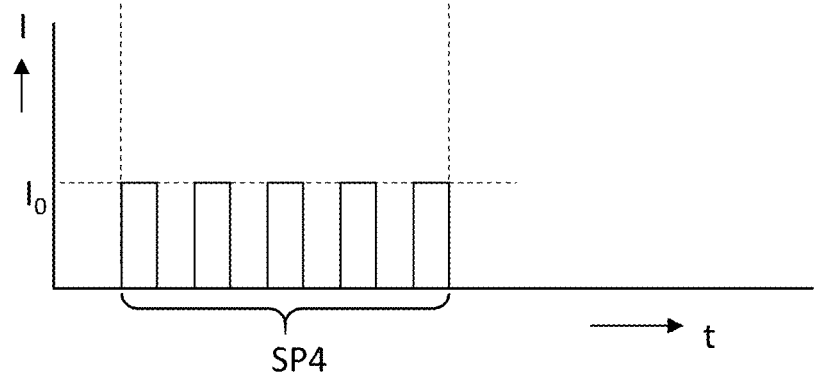

FIG. 8D shows a time-course of the intensity for a stimulation period SP4. This time-course differs from the time-course of FIG. 8A in that the frequency with which the stimulus is provided is higher than in FIG. 8A. However, the intensity with which the stimulus is provided is the same, $I_0$, and the duration of the stimulation period is also the same, i.e. SP1 is as long as SP4.

As explained above, the total surface area below the intensity-time graphs in FIGS. 8A-8D are indicative of the total energy of the stimulus for the respective stimulation periods SP1-SP4. The total surface area below the intensity-time graphs for each of the graphs B, C and D is larger than the total surface area below the intensity-time graph of A. Herewith, FIG. 8A-8D illustrates that, without any other measures, changing the intensity, duration or frequency of a stimulus involves changing, typically increasing, the total energy of the stimulus during the stimulation period.

FIGS. 9A-9F illustrates six irregular time-courses A-F of the stimulus intensity during a stimulation period.

Figure 9A:
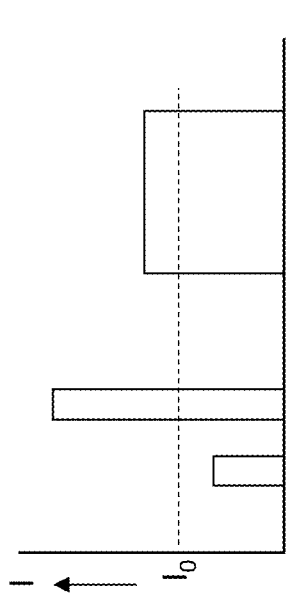
FIGS. 9A, 9B, 9C, 9D, 9E, and 9F shows irregular time-courses for a stimulus intensity.

In time-course shown in FIG. 9A, the stimulus generator 6 is caused to subsequently be in the on-state during sub-period a, in the off-state during sub-period b and in the on-state during sub-period c. In this example, sub-period a is shorter than sub-period c. Hence, the intensity may be understood to vary irregularly.

Figure 9B:
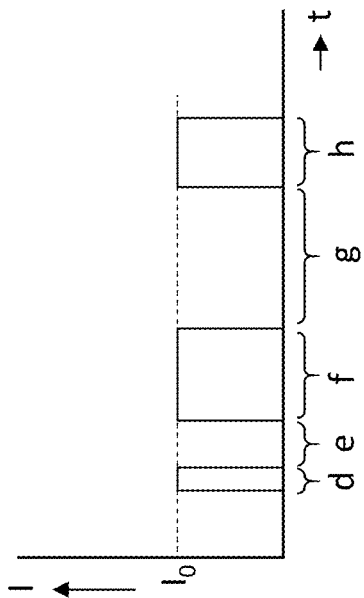

Time-course shown in FIG. 9B illustrates that the intensity can vary irregularly also if the stimulus generator is not in an off-state during the stimulation period.

Figure 9C:
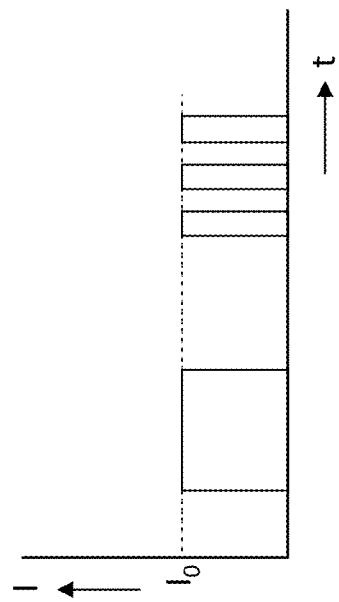

Time-course shown in FIG. 9C illustrates that the intensity can vary during distinct on-states. Thus, even if the on and off-states occur at regular intervals, then still the intensity can vary irregularly as shown.

Figure 9D:
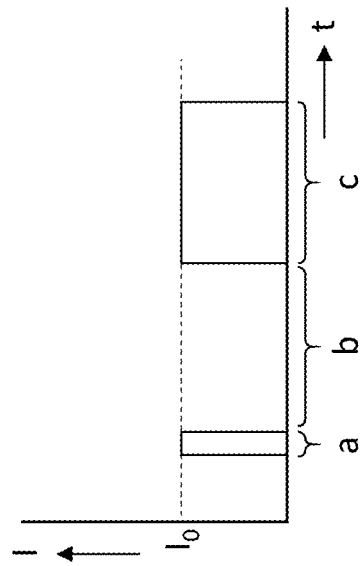

Time-course shown in FIG. 9D illustrates that the intensity may have constant values during respective on-states, however, that these constant values can be different for the respective on-states.

Figure 9E:
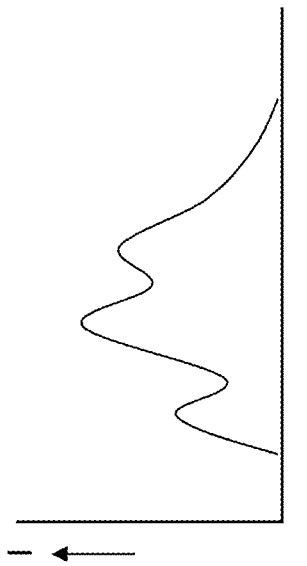

Time-course shown in FIG. 9E comprises five sub-periods d-h. During sub-periods d, f, h, the stimulus generator is in the on-state. During sub-periods e, g the stimulus generator is in the off-state. In this example, the intensity varies irregularly because sub-period e is shorter than sub-period g.

Figure 9F:
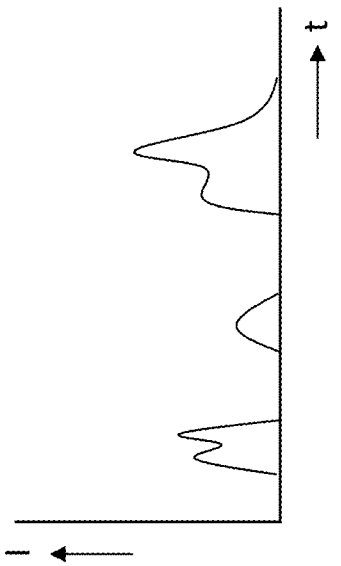
Figure 10:
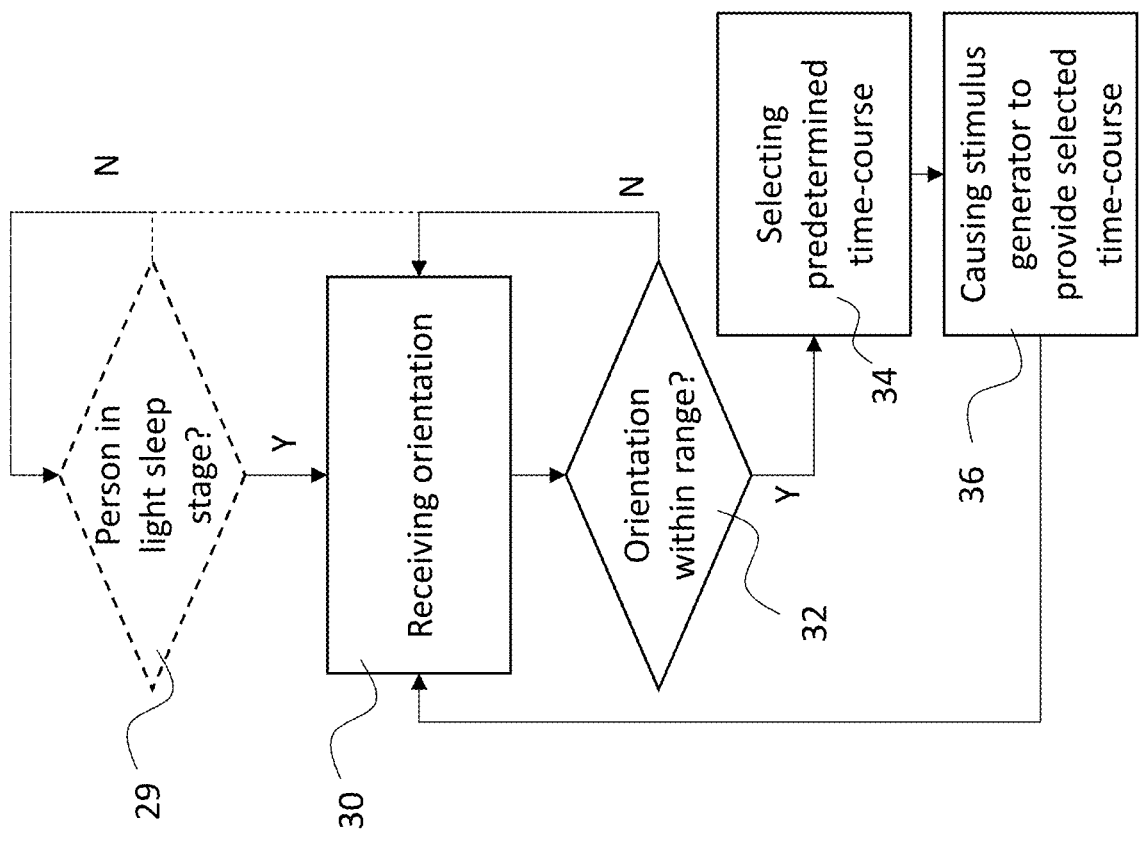
FIG. 10 illustrates a method according to an embodiment.

Time-course shown in FIG. 9F illustrates yet another example of an irregularly varying intensity during a stimulation period.

FIG. 6A illustrates an algorithm that may be followed by the sleep position training device 2, in particular by the processing system 100. Optionally, the processing system 100 is configured to perform a step 29 of determining that the person is in a light sleep stage of a sleep cycle. This is beneficial because the stimuli can be provided when the person is in a light sleep stage.

Step 29 may be performed by determining the RRV as illustrated in FIG. 6A.

If the processing system 100 determines in step 29 that the person is not in a light sleep stage, it may wait for a predetermined time before it executes step 29 again.

Then, step 30 comprises the processing system 100 receiving an orientation signal from the orientation sensor 4 as described above.

Then, the processing system performs step 32 which comprises determining whether the orientation of the torso is within the predetermined orientation range or not. If this is not the case, then step 30 (or step 29) is performed again.

If the processing system 100 in step 32 determines that the orientation is within the orientation range, it will perform step 34, which comprises selecting, for example randomly selecting, a particular time-course out of the plurality of time-courses. This plurality of time-courses was stored by the processing system 100 beforehand.

Then, in step 36, the processing system 100 causes the stimulus generator to provide the stimulus in accordance with the selected time-course.

In some embodiments, the subsequent stimulation periods SP are separated in time by at least a wait period, such as one minute, in order to reduce the risk of waking the person.

If step 29 was indeed performed, then it should be appreciated that the stimulus generator is caused to provide the stimulus in step 36 based on both the determination that was made in step 29 and based on the determination that was made in step 32.

FIG. 11 depicts a block diagram illustrating an exemplary processing system according to an embodiment. As shown in FIG. 11, the processing system 100 may include at least one processor 102 coupled to memory elements 104 through a system bus 106. As such, the processing system may store program code within memory elements 104. Further, the processor 102 may execute the program code accessed from the memory elements 104 via a system bus 106. In one aspect, the processing system may be implemented as a computer that is suitable for storing and/or executing program code. It should be appreciated, however, that the processing system 100 may be implemented in the form of any system including a processor and a memory that is capable of performing the functions described within this specification.

The memory elements 104 may include one or more physical memory devices such as, for example, local memory 108 and one or more bulk storage devices 110. The local memory may refer to random access memory or other non-persistent memory device(s) generally used during actual execution of the program code. A bulk storage device may be implemented as a hard drive or other persistent data storage device. The processing system 100 may also include one or more cache memories (not shown) that provide temporary storage of at least some program code in order to reduce the number of times program code must be retrieved from the bulk storage device 110 during execution.

Input/output (I/O) devices depicted as an input device 112 and an output device 114 optionally can be coupled to the processing system. Examples of input devices may include, but are not limited to, a keyboard, a pointing device such as a mouse, or the like. Examples of output devices may include, but are not limited to, a monitor or a display, speakers, or the like. Input and/or output devices may be coupled to the processing system either directly or through intervening I/O controllers.

In some embodiments, the input and the output devices may be implemented as a combined input/output device (illustrated in FIGS. 7A-7C with a dashed line surrounding the input device 112 and the output device 114). An example of such a combined device is a touch sensitive display, also sometimes referred to as a "touch screen display" or simply "touch screen". In some embodiments, input to the device may be provided by a movement of a physical object, such as e.g. a stylus or a finger of a person, on or near the touch screen display.

A network adapter 116 may also be coupled to the processing system to enable it to become coupled to other systems, computer systems, remote network devices, and/or remote storage devices through intervening private or public networks. The network adapter may comprise a data receiver for receiving data that is transmitted by said systems, devices and/or networks to the processing system 100, and a data transmitter for transmitting data from the processing system 100 to said systems, devices and/or networks. Modems, cable modems, and Ethernet cards are examples of different types of network adapter that may be used with the processing system 100.

As pictured in FIG. 11, the memory elements 104 may store an application 118. In various embodiments, the application 118 may be stored in the local memory 108, the one or more bulk storage devices 110, or apart from the local memory and the bulk storage devices. It should be appreciated that the processing system 100 may further execute an operating system (not shown in FIGS. 7A-7C) that can facilitate execution of the application 118. The application 118, being implemented in the form of executable program code, can be executed by the processing system 100, e.g., by the processor 102. Responsive to executing the application, the processing system 100 may be configured to perform one or more operations or method steps described herein.

In one aspect, the processing system 100 can represent a control module for the sleep position training device as described herein.

Various embodiments may be implemented as a program product for use with a computer system, where the program(s) of the program product define functions of the embodiments (including the methods described herein). In one embodiment, the program(s) can be contained on a variety of non-transitory computer-readable storage media, where, as used herein, the expression "non-transitory computer readable storage media" comprises all computer-readable media, with the sole exception being a transitory, propagating signal. In another embodiment, the program(s) can be contained on a variety of transitory computer-readable storage media. Illustrative computer-readable storage media include, but are not limited to: (i) non-writable storage media (e.g., read-only memory devices within a computer such as CD-ROM disks readable by a CD-ROM drive, ROM chips or any type of solid-state non-volatile semiconductor memory) on which information is permanently stored; and (ii) writable storage media (e.g., flash memory, floppy disks within a diskette drive or hard-disk drive or any type of solid-state random-access semiconductor memory) on which alterable information is stored. The computer program may be run on the processor 102 described herein.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of embodiments of the present disclosure has been presented for purposes of illustration, but is not intended to be exhaustive or limited to the implementations in the form disclosed. Many modifications and variations will be apparent to those of ordinary skill in the art without departing from the scope of the claims. The embodiments were chosen and described in order to best explain the principles and some practical applications of the present disclosure, and to enable others of ordinary skill in the art to understand the present disclosure for various embodiments with various modifications as are suited to the particular use contemplated.

Where applicable, all individual characteristics illustrated in the embodiment example can be combined with and/or exchanged for each other without departing from the scope of the disclosure.

All patents, patent applications, and published references cited herein are hereby incorporated by reference in their entirety. It will be appreciated that several of the above-disclosed and other features and functions, or alternatives thereof, may be desirably combined into many other different systems or application. Various alternatives, modifications, variations, or improvements therein may be subsequently made by those skilled in the art.

The invention claimed is:

1. A sleep position training device comprising:
an orientation sensor configured to output a signal indicative of an orientation of a torso of a person,
a stimulus generator configured to provide a stimulus to the person, wherein the stimulus generator is affixable to the person, and
a processing system configured to perform steps of:
receiving a signal from the orientation sensor, the signal being indicative of an orientation of the torso of the person,
determining on a basis of the signal that the orientation of the torso of the person is within a predetermined torso orientation range in a sleeping position of the person, and
instructing the stimulus generator:
i) to provide the stimulus to the person to reduce gastroesophageal reflux in the sleeping position of the person when the orientation of the torso of the person is at an angle greater than or equal to 30 degrees in an upper right quadrant (XZ-1) of an x-z plane with respect to a z-axis of the x-z plane, wherein the x-z plane is perpendicular to a longitudinal axis of the torso of the person in a supine position in a y-direction, or ii) not to provide the stimulus when the orientation of the torso of the person is at an angle less than 30 degrees in the upper right quadrant (XZ-1) of the x-z plane with respect to the z-axis of the x-z plane, or is in at least a part of an upper left quadrant (XZ-2) of the x-z plane, wherein the upper right and upper left quadrants are viewed in the y-direction along the longitudinal axis from the torso to feet of the person.

2. The sleep position training device according to claim 1, wherein the predetermined torso orientation range is such that the processing system is further configured to perform a step of instructing the stimulus generator to provide the stimulus when the orientation of the torso of the person is in a part of the upper left quadrant (XZ-2) of the x-z plane, in at least a part of a lower right quadrant (XZ-4) of the x-z plane, or both.

3. The sleep position training device according to claim 1, wherein the predetermined torso orientation range is such that the processing system is further configured to perform a step of instructing the stimulus generator to provide the stimulus when the orientation of the torso of the person is in an entire lower right quadrant (XZ-4) of the x-z plane.

4. The sleep position training device according to claim 3, wherein the predetermined torso orientation range is such that the processing system is further configured to perform a step of instructing the stimulus generator to provide the stimulus when the orientation of the torso of the person is in the upper right quadrant (XZ-1) and the lower right quadrant (XZ-4) over an angle larger than 120 degrees.

5. The sleep position training device according to claim 1, wherein the predetermined torso orientation range is such that in an y-z plane, perpendicular to the x-z plane, the processing system is further configured to perform a step of instructing the stimulus generator not to provide the stimulus when the orientation of the torso of the person is in at least a part of at least one of an upper left quadrant (YZ-2) of the y-z plane and an upper right quadrant (YZ-1) in the y-z plane.

6. The sleep position training device according to claim 1, wherein the sleep position training device comprises an orientation means for affixing the device to the torso of the person in a correct orientation.

7. The sleep position training device according to claim 1, wherein the processing system is configured to trigger the stimulus generator to provide the stimulus when the torso of the person is in the predetermined torso orientation range only after a time duration.

8. The sleep position training device according to claim 1, wherein the processing system is configured to perform steps of:
receiving an additional signal from the orientation sensor, the additional signal being indicative of an additional orientation of the torso of the person, and
determining on the basis of the additional signal that the additional orientation of the torso of the person is within the predetermined torso orientation range, and, based on this determination, causing the stimulus generator to provide an additional stimulus that is different from the stimulus.

9. The sleep position training device according to claim 8, wherein an intensity of the stimulus has a time course during a stimulation period, wherein the time course is irregular.

10. The sleep position training device according to claim 9, wherein, the intensity of the additional stimulus has an additional time-course during an additional stimulation period and wherein the additional time-course differs from the time-course, wherein, optionally, the additional time course is irregular.

11. The sleep position training device according to claim 1, wherein the sleep position training device is affixable to an upper part of the torso of a person, the device further comprising:
an accelerometer configured to output an acceleration signal, wherein the processing system is configured for:
receiving the acceleration signal from the accelerometer and to derive a respiratory rate variability of the person, and
instructing the stimulus generator to provide the stimulus to the person when the person is in the predetermined orientation range in a sleeping position, wherein the stimulus is provided dependent on the respiratory rate variability derived by the processing system.

12. The sleep position training device according to claim 8, wherein the processing system is configured for comparing a derived respiratory rate variability with at least one variability threshold set to distinguish between a first sleep stage and a second sleep stage of the person, wherein the processing system is configured to:
trigger the stimulus generator to provide the stimulus when the person is in the first sleep stage, and
not trigger the stimulus generator to provide the stimulus when the person is in the second sleep stage.

13. The sleep position training device according to claim 8, wherein an accelerometer is used as the orientation sensor of the sleep position training device.

14. A sleep position training device comprising:
an orientation sensor configured to output a signal indicative of an orientation of a torso of a person,
a stimulus generator configured to provide a stimulus to the person, wherein the stimulus generator is affixable to the torso of the person, and
a processing system configured to perform steps of:
receiving a signal from the orientation sensor, the signal being indicative of an orientation of the torso of the person,
determining on a basis of the signal that the orientation of the torso of the person is within a predetermined torso orientation range in a sleeping position of the person, and
instructing the stimulus generator:
i.) to provide the stimulus to the person to reduce gastroesophageal reflux in the sleeping position of the person when the orientation of the torso of the person is in a part of an upper right quadrant (XZ-1) of an x-z plane with respect to a z-axis of the x-z plane, wherein the x-z plane is perpendicular to a longitudinal axis of the torso of the person in a supine position in a y-direction, or
ii.) not to provide the stimulus when the orientation of the torso of the person is at an angle less than 30 degrees in the upper right quadrant (XZ-1) of the x-z plane with respect to the z-axis of the x-z plane, or is in at least a part of an upper left quadrant (XZ-2) of the x-z plane, wherein:

the upper right and upper left quadrants are viewed in the y-direction along the longitudinal axis from the torso to feet of the person, and the stimulus is provided for a larger part of the upper right quadrant (XZ-1) of the x-z plane than for the upper left quadrant (XZ-2) of the x-z plane.

15. The sleep position training device according to claim 14, wherein the predetermined torso orientation range is such that the processing system is further configured to perform a step of instructing the stimulus generator to provide the stimulus when the orientation of the torso of the person is in at least a part of a lower right quadrant (XZ-4) of the x-z plane.

16. The sleep position training device according to claim 15, wherein the predetermined torso orientation range is such that the processing system is further configured to perform a step of instructing the stimulus generator to provide the stimulus when the orientation of the torso of the person is in the upper right quadrant (XZ-1) and the lower right quadrant (XZ-4) over an angle larger than 120 degrees.

17. The sleep position training device according to claim 14, wherein the predetermined torso orientation range is such that in an y-z plane, perpendicular to the x-z plane, the processing system is further configured to perform a step of instructing the stimulus generator not to provide the stimulus when the orientation of the torso of the person is in at least a part of at least one of an upper left quadrant (YZ-2) of the y-z plane and an upper right quadrant (YZ-1) in the y-z plane.

18. The sleep position training device according to claim 1, wherein the stimulus is provided to the torso of the person.

19. The sleep position training device according to claim 14, wherein the stimulus is provided to the torso of the person.

* * * * *